United States Patent [19]
Wels et al.

[11] Patent Number: 5,942,602
[45] Date of Patent: Aug. 24, 1999

[54] GROWTH FACTOR RECEPTOR ANTIBODIES

[75] Inventors: Winfried S. Wels, Emmendingen; Mathias Schmidt, Freiburg; Evangelia Vakalopoulou, Berlin, all of Germany; Douglas W Schneider, Lafayette, Calif.

[73] Assignee: Schering Aktiengessellschaft, Berlin, Germany

[21] Appl. No.: 08/800,198

[22] Filed: Feb. 13, 1997

[51] Int. Cl.⁶ .............................. C07K 16/28; C07K 16/30
[52] U.S. Cl. ................... 530/388.22; 530/388.8; 530/388.85; 530/391.3; 530/391.7; 530/387.3; 536/23.1; 536/24.31; 424/9; 424/178.1
[58] Field of Search ............................ 530/388.22, 388.8, 530/388.85, 391.3, 391.7, 387.3; 536/23.1, 24.31; 424/9, 178.1

[56] References Cited

FOREIGN PATENT DOCUMENTS

| 645 747 | 11/1990 | Australia . |
| 0 586 002 | 3/1994 | European Pat. Off. . |
| 0 739 984 | 10/1996 | European Pat. Off. . |

OTHER PUBLICATIONS

Lorimer et al., PNAS 93:14815–14820 (1996).

Wikstrand et al., Cancer Research 55:3140–3148 (1995).

Schmidt et al., Brit. J. Cancer 75:1575–1584 (1997).

Wels et al., *International Journal of Cancer*, vol. 60, No. 1, pp. 137–144, Jan. 3, 1995.

*Primary Examiner*—Toni R. Scheiner
*Attorney, Agent, or Firm*—Millen, White, Zelano & Branigan, P.C.

[57] ABSTRACT

The present invention is related to single and double chain antibodies to EGF receptor. The invention also relates to toxin conjugates of such antibodies. These antibodies are useful for treating and diagnosing the status of pathological conditions such as cancer and cellular hyper proliferation.

25 Claims, 13 Drawing Sheets

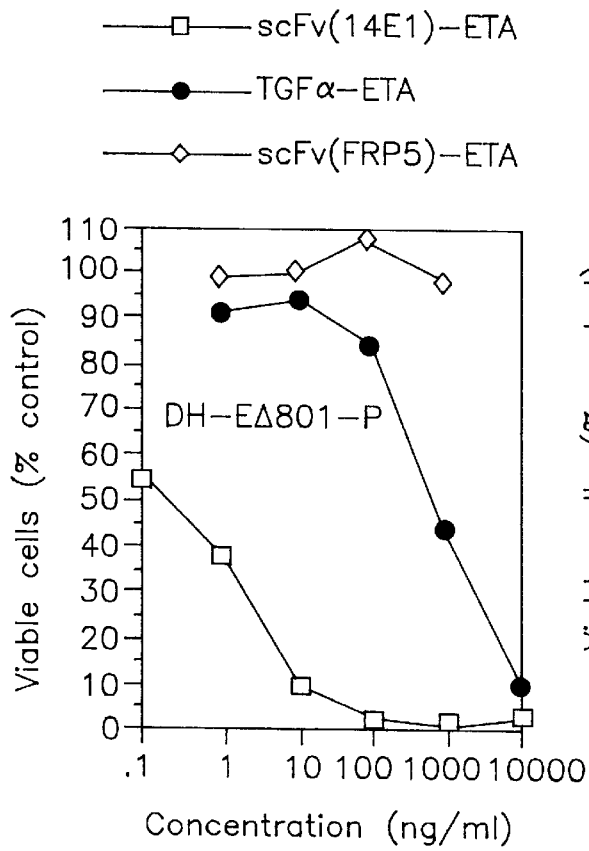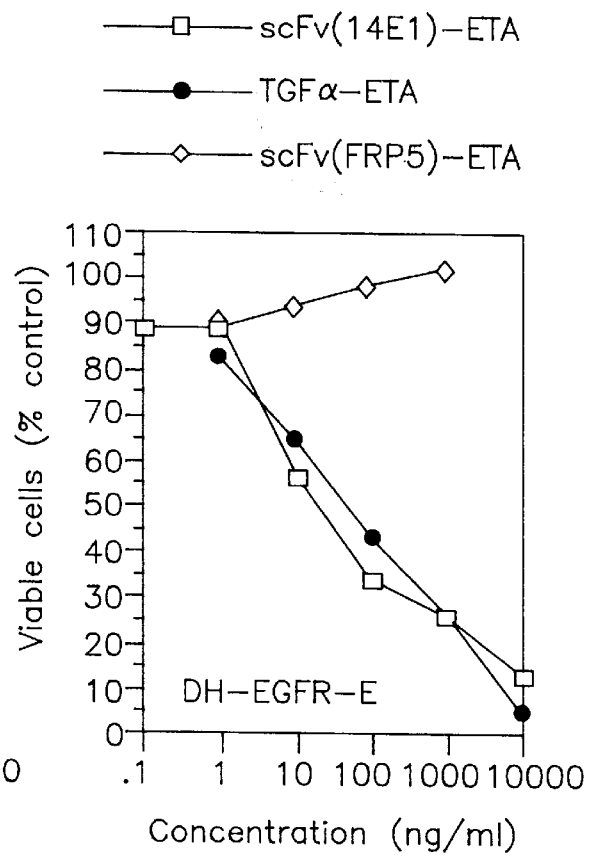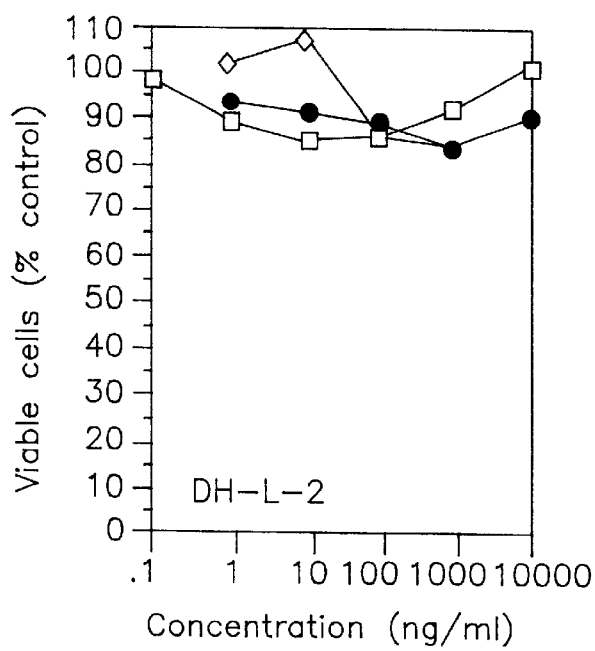
FIG. 7A
FIG. 7B
FIG. 7C

FIG. 9A
Sequence 1
VH 14E1

```
CAGGTGCAGC TGCAGGAGTC TGGGGCTGAA CTGGCAAAAC CTGGGGCCTC AGTGAAGATG TCCTGCAAGG CTTCTGGCTA   80
CACCTTTACT AACTACTGGA TGCACTGGGT GACACAGAGG CCTGGACAGG TGCTGGTATG GATTGGATAC ACTAATCCTA  160
ACACTGGTTA TACTGATTTC AATCAGAAGT TCAAGGACAA GGCCACATTG ACTGCAGACA AATCCTCCAG CACAGCCTAC  240
ATGCAACTGA GCGGCCTGAC ATCTGAGGAC TCTGCAGTCT ATTACTGTGC AAGAGGGGAT TACTACGGCT ACGACTTTGC  320
TTACTGGGGC CAAGGGACCA CGGTCACCGT TTCCTCT                                                  357
```

FIG. 9B
Sequence 2
VH 14E1

```
QVQLQESGAE LAKPGASVKM SCKASGYTFT NYWMHWVTQR PGQVLVWIGY TNPNTGYTDF NQKFKDKATL TADKSSSTAY   80
MQLSGLTSED SAVYYCARGD YYGYDFAYWG QGTTVTVSS                                                119
```

FIG. 9C
Sequence 3
VH14E1

```
GACATCCAGC TGACCCAGTC TCCAGCCATC CTGTCTGTGA GTCCAGGAGA AAGAGTCAGT TTCTCCTGCA GGGCCAGTCA   80
GAGCATTGGC ACAAATATAC ACTGGTATCA GCAAAGAACA AATGGTTCTC CAAGGCTTCT CATAAAGTAT GCTTCTGAGT  160
CTATCTCTGG GATCCCTTCC AGGTTTAGTG GCAGTGGATC AGGGACAGAT TTTACTCTTA GCATCAACAG TGTGGAGTCT  240
GCAGATATTG CAGATTATTA CTGTCAACAA GTTGATAGCT AGTGATAGCT CTCGGTGCT GGGACAAAGC TCGAGATT    318
```

FIG. 9D

Sequence 4
VL 14E1 (VL #2)

```
DIQLTQSPAI LSVSPGERVS FSCRASQSIG TNIHWYQQRT NGSPRLLIKY ASESISGIPS RFSGSGSGTD FTLSINSVES   80
ADIADYYCQQ SDSWPTTFGA GTKLEI                                                            106
```

FIG. 9E

Sequence 5
VL 14E1

```
GACATTGAGC TCACCCAGTC TCCATCCTCC CTGACTGTGG CAGCAGGAGA GAAGGTCACT ATGAGCTGCA AGTCCAGTCA   80
GAGTCTCTTA GCTAGTGGCA ACCAACTAGG CTACTTGGCC TGGCACCAGG AGAAACCAGG ACGATCTCCT AAAATGCTGA  160
TAATTTGGGC ATCCACTAGG GTTTCTGGAG TCCCTGATCG CTTCATAGGC AGTGGATCTG GGACGGATTT CACTCTGACC  240
ATCAACAGTG TGCAGGCTGA AGATCTGGCT GTTTATTACT GTCAGCAGTC CTACAGCGCT CTCACGTTCG GTGCTGGCAC  320
CAAGCTGGAA ATC                                                                          333
```

FIG. 9F

Sequence 6
VL 14E1 (VL #1)

```
DIELTQSPSS LTVAAGEKVT MSCKSSQSLL ASGNQNNYLA WHQQKPGRSP KMLIIWASTR VSGVPDRFIG SGSGTDFTLT   80
INSVQAEDLA VYYCQQSYSA LTFGAGTKLE I                                                      131
```

FIG. 9G

Sequence 7
scFv(14E1)

```
CAGGTGCAGC TGCAGGAGTC TGGGGCTGAA CTGGCAAAAC CTGGGGCCTC AGTGAAGATG TCCTGCAAGG CTTCTGGCTA    80
CACCTTTACT AACTACTGGA TGCACTGGGT TCAAGGACAG CCTGGACAGG GCCTGGATAT ACTAATCCTA    160
ACACTGGTTA TACTGATTTC AATCAGAAGT TCAAGGACAA GGCCACATTG ACTGCAGACA AATCCTCCAG CACAGCCTAC    240
ATGCAACTGA GCGGCCTGAC ATCTGAGGAC TCTGCAGTCT ATTACTGTGC AAGAGGGGAT TACTACGGCT ACGACTTTGC    320
TTACTGGGGC CAAGGGACCA CGGTCACCGT TTCCTCTGGC GGTGGCGGCT CTGGTGGCGG TGGCTCCGGC GGTGGCGGTT    400
CTGACATCCA GCTGACCCAG TCTCCAGCCA TCCTGTCTGT GAGTCCAGGA GAAAGAGTCA GTTTCTCCTG CAGGGCCAGT    480
CAGAGCATTG GCACAAATAT ACACTGGTAT CAGCAAAGAA CAAATGGTTC TCCAAGGCTT CTCATAAAGT ATGCTTCTGA    560
GTCTATCTCT GGGATCCCTT CCAGGTTTAG TGGCAGTGGA TCAGGGACAG ATTTTACTCT TAGCATCAAC AGTGTGGAGT    640
CTGAGGATAT TGCAGATTAT TACTGTCAAC AAAGTGATAG CTGGCCAACC ACGTTCGGTG CTGGGACAAA GCTCGAGATT    720
```

FIG. 9H

Sequence 8
scFv(14E1)

```
QVQLQESGAE LAKPGASVKM SCKASGYTFT NYWMHWVTQR PGQVLVWIGY TNPNTGYTDF NQKFKDKATL TADKSSSTAY    80
MQLSGLTSED SAVYYCARGD YYGYDFAYWG QGTTVTVSSG GGGSGGGGSG GGGSDIQLTQ SPAILSVSPG ERVSFSCRAS    160
QSIGTNIHWY QQRTNGSPRL LIKYASESIS GIPSRFSGSG SGTDFTLSIN SVESADIADY YCQQSDSWPT TFGAGTKLEI    240
```

```
DNA sequence      720 b.p.      CAGGTGCAGCTG...AAGCTCGAGATT   linear

1/1                                                  31/11
CAG GTG CAG CTG CAG GAG TCT GGG GCT GAA CTG GCA AAA CCT GGG GCC TCA GTG AAG ATG
 Q   V   Q   L   Q   E   S   G   A   E   L   A   K   P   G   A   S   V   K   M

61/21                                                91/31  CDR1
TCC TGC AAG GCT TCT GGC TAC ACC TTT ACT AAC TAC TGG ATG CAC TGG GTG ACA CAG AGG
 S   C   K   A   S   G   Y   T   F   T  |N   Y   W   M   H| W   V   T   Q   R

121/41                                               151/51                CDR2
CCT GGA CAG GTG CTG GTA TGG ATT GGA TAC ATT AAT CCT AAC ACT GGT TAT ACT GAT TTC
 P   G   Q   V   L   V   W   I   G  |Y   I   N   P   N   T   G   Y   T   D   F

181/61                                               211/71
AAT CAG AAG TTC AAG GAC AAG GCC ACA TTG ACT GCA GAC AAA TCC TCC AGC ACA GCC TAC
 N   Q   K   F   K   D| K   A   T   L   T   A   D   K   S   S   S   T   A   Y

241/81                                               271/91                CDR3
ATG CAA CTG AGC GGC CTG ACA TCT GAG GAC TCT GCA GTC TAT TAC TGT GCA AGA GGG GAT
 M   Q   L   S   G   L   T   S   E   D   S   A   V   Y   Y   C   A   R  |G   D

301/101                                              331/111                          VH
TAC TAC GGC TAC TAC GAC TTT GCT TAC TGG GGC CAA GGG ACC ACG GTC ACC GTT TCC TCT|GGC
 Y   Y   G   Y   Y   D   F   A   Y| W   G   Q   G   T   T   V   T   V   S   S   G
                                                                           Synth. Linker
```

FIG. 10A

```
                                                              VL (#2)
                                                        CDR1
361/121
GGT GGC GGT TCT GGT GGC GGT GGC TCC GGC GGT TCT GAC ATC CAG CTG ACC CAG
 G   G   G   S   G   G   G   G   S   G   G   S   D   I   Q   L   T   Q

421/141
TCT CCA GCC ATC CTG TCT GTG TCT CCA GGA GAA AGA GTC AGT TTC TCC TGC AGG GCC AGT
 S   P   A   I   L   S   V   S   P   G   E   R   V   S   F   S   C   R   A   S

481/161
CAG AGC ATT GGC ACA AAT ATA CAC TGG TAT CAG CAA AGA ACA AAT GGT TCT CCA AGG CTT
 Q   S   I   G   T   N   I   H   W   Y   Q   Q   R   T   N   G   S   P   R   L

CDR2
541/181
CTC ATA AAG TAT GCT TCT GAG TCT ATC TCT GGG ATC CCT TCC AGG TTT AGT GGC AGT GGA
 L   I   K   Y   A   S   E   S   I   S   G   I   P   S   R   F   S   G   S   G

601/201
TCA GGG ACA GAT TTT ACT CTT AGC ATC AAC AGT GTG GAG TCT GCA GAT ATT GCA GAT TAT
 S   G   T   D   F   T   L   S   I   N   S   V   E   S   A   D   I   A   D   Y

CDR3
661/221
TAC TGT CAA CAA AGT GAT AGC TGG CCA ACC ACG TTC GGT GCT GGG ACA AAG CTC GAG ATT
 Y   C   Q   Q   S   D   S   W   P   T   T   F   G   A   G   T   K   L   E   I
```

FIG. 10B

GROWTH FACTOR RECEPTOR ANTIBODIES

FIELD OF THE INVENTION

The present invention is related to a novel single chain antibody-toxin, scFv(14E1)-ETA, based on the independently isolated EGF receptor specific monoclonal antibody 14E1.

BACKGROUND OF THE INVENTION

The erbB/EGF receptor related gene family encodes growth factor receptors with intrinsic tyrosine kinase activity. Four members of this family have been identified: ErbB/EGF receptor, ErbB-2, ErbB-3 and ErbB-4 (reviewed in Peles and Yarden, 1993). Members of this family have been implicated in the development of a variety of human malignancies. EGF receptor gene amplification and overexpression has been observed in a high percentage of primary human carcinomas of epithelial origin including glioblastoma, cancer of the lung, breast, head and neck, and bladder, and correlates with an unfavorable prognosis for the patients (reviewed in Gullick, 1991). Increased receptor expression in tumor cells is often accompanied by increased production of TGFα (Derynck et al., 1987), which leads to receptor activation by an autocrine pathway and contributes to malignant transformation. Due to its accessibility on the cell surface, its overexpression in several types of cancer, and its involvement as a marker for an unfavorable prognosis, the EGF receptor and/or its variants (Ekstrand, A. J., Longo, N., Hamid, M. L., Olson, J. J., Liu, L., Collins, V. P., and James, C. D. Functional characterization of an EGF receptor with a truncated extracellular domain expressed in glioblastomas with EGFR gene amplification. Oncogene, 9: 2313–2320, 1994; Sugawa, N., Ekstrand, A. J., James, C. D., and Collins, V. P. Identical splicing of aberrant epidermal growth factor receptor transcripts from amplified rearranged genes in human glioblastomas. Proc. Natl. Acad. Sci. USA, 87: 8602–6, 1990; Wong, A. J., Ruppert, J. M., Bigner, S. H., Grzeschik, C. H., Humphrey, P. A., Bigner, D. S., and Vogelstein, B. Structural alterations of the epidermal growth factor receptor gene in human gliomas. Proc. Natl. Acad. Sci. USA, 89: 2965–9, 1992; Yamazaki, H., Ohba, Y., Tamaoki, N., and Shibuya, M. A deletion mutation within the ligand binding domain is responsible for activation of epidermal growth factor receptor gene in human brain tumors. Jpn. J. Cancer Res., 81: 773–9, 1990; Wikstrand, C. J., Hale, L. P., Batra, S. K., Hill, M. L., Humphrey, P. A., Kurpad, S. N., McLendon, R. E., Moscatello, D., Pegram, C. N., Reist, C. J., and et al Monoclonal antibodies against EGFRvIII are tumor specific and react with breast and lung carcinomas and malignant gliomas. Cancer Res., 55: 3140–3148, 1995; Moscatello, D. K., Holgado-Madruga, M., Godwin, A. K., Ramirez, G., Gunn, G., Zoltick P. W., Biegel, J. A., Hayes, R L., and Wong, A. J. Frequent expression of a mutant epidermal growth factor receptor in multiple human tumors. Cancer Res., 55: 5536–9, 1995; Hills, D., Rowlinson-Busza, G., and Gullick, W. J. Specific targeting of a mutant, activated EGF receptor found in glioblastoma using a monoclonal antibody. Int. J. Cancer, 63: 537–543, 1995) are under intensive scrutiny as a therapeutic target for novel antitumor reagents.

Various strategies have been employed to target the EGF receptor and/or his variants for tumor therapy. Monoclonal antibodies directed towards the extracellular domain of the EGF receptor have proven effective in the inhibition of tumor cell growth. The EGF receptor specific Mab 225 competes with EGF for binding to the EGF receptor thereby blocking ligand dependent receptor activation (Fan et al, 1993). Treatment with Mab 225 inhibits the growth of EGF receptor expressing tumor cells in vitro and in animal models in vivo (Masui et al., 1984; Ennis et al., 1989), and clinical studies with Mab 225 have recently been initiated. In an attempt to achieve more potent antitumoral effects recombinant fusion proteins have been constructed which contain the enzymatic domains of *Pseudomonas exotoxin A* (Chaudhary et al., 1987) or diphtheria toxin (Shaw et al., 1991), and employ the natural EGF receptor ligands TGFα or EGF for targeting to receptor overexpressing tumor cells. Due to the growth factor domain such toxins are able to activate the EGF receptor (Schmidt and Wels, 1996), which might facilitate rapid uptake by tumor cells, but could also be responsible for the significant cytotoxic activity displayed on cells expressing only moderate levels of the target receptor.

As an alternative to growth factors, single-chain immunotoxin (SCIT) fusion proteins can be used for the target cell specific delivery of therapeutic effector functions. SCIT fusion proteins are hybrid molecules that contain antibody variable regions (scFv) genetically fused to a binding defective toxin, most notably diphteria toxin (DT) and *Pseudomonas exotoxin A* (ETA). Both DT and PE halt protein synthesis by ADP-ribosylating elongation factor 2 upon entry to the cell cytosol resulting in cell death (Carroll and Collier, 1987). A recombinant single chain antibody-toxin consisting of a scFv domain derived from the antagonistic Mab 225 and truncated *Pseudomonas exotoxin* A was described recently (Wels et al., 1995).

SUMMARY OF THE INVENTION

It is an object of the invention to provide an EGF receptor specific single chain antibody comprising a Vlight and Vheavy chain which is highly specific for tumor cells expressing, especially overexpressing, the EGP receptor and/or EGF receptor variants for example EGFRvIII. In accordance with the invention, the single chain antibody or polypeptide can comprise a Vlight chain having the characteristics of monoclonal antibody 14E1, e.g., sequences 3, 4, 5 and 6, and a Vheavy chain having the characteristics of monoclonal antibody 14E 1, e.g., sequences 1 and 2. The antibody can be conjugated or joined to a biologically-active component or diagnostic agent for therapeutic and diagnostic purposes. For example, the antibody can be joined to a cytotoxin, such as ETA, to achieve a highly potent cell killing activity. It is a further object of the invention to provide a pharmaceutical composition containing an effective amount of the mentioned single chain antibody as an active component and a non-toxic pharmaceutical carrier or solution.

It is another aspect of the invention to provide a test kit comprising an EGF receptor and/or EGF receptor variants specific single chain antibody as mentioned above, e.g., conjugated or joined to a biologically-active component such as ETA, or conjugated to a MRI contrast agent, a radiodiagnostic agent, or a radiotherapeutic agent. By biologically active, it is meant that the component has an effect in a biological system, either on an in vitro or in vivo system. Biologically-active components includes, e.g., cytotoxins such as ETA or diphteria toxin, cytokines such as interferons (α-, β- and γ), interleukins, TNF-α, Rantes, MIP, hormones, estrogens, growth factors, etc. See, e.g., Siegall et al., Drug Development Research, 34:210–219, 1995 for other cytotoxins or immunotoxins. The biologically-active component can be covalently joined to the antibody, or noncovalently joined, e.g., by hydrogen or ionic bonds. If the biologically-active component is a peptide, it can be fused in-frame to the single chain polypeptide in a continous reading frame as illustrated in the example below for ETA. The single chain polypeptide can also comprise a radiodiagnostic or radiotherapeutic agent or a MRI contrast agent (for reference see for example DE-OS 37 10730 A1, European Patent Application 0512661A1, DE-OS 43 37 600 A1, DE-OS 43 13 670 A1 and DE-OS 43 37 599 A1). An agent can be an atom, a molecule, a compound, a chelate, etc., or any substance which is effective for these purposes. A radiodiagnostic agent can be, e.g., a radioactive isotope complexed with a chelate. A MRI agent comprises, e.g., a paramagnetic ion. A single chain polypeptide in accordance with the present invention also includes polypeptides which have the characteristics of monoclonal antibody 14E1. By the phrase "has the characteristics of," it is meant that the polypeptide binds to the same epitope or to a mimetope which is also specifically recognized by mAb 14E1. The polypeptide can also have substantially the same binding affinity and/or tissue specificity and/or amino acid sequence of monoclonal antibody 14E1.

The present invention also includes a double-chain polypeptide having a binding affinity for an epidermal growth factor receptor and/or its variants, said polypeptide comprising: (1) a first polypeptide segment comprising the binding portion of the heavy chain variable domain of monoclonal antibody 14E1; and (2) a second polypeptide segment comprising the binding portion of the light chain variable domain of monoclonal antibody 14E1, where (1) and (2) are joined by other than peptide sequences, e.g., cysteine bonds. See, e.g. Reiter et i., Nature Biotechnology, 14:1239–1245, 1996. The binding portion is the part of the polypeptide segment which recognizes the desired epitope.

The present invention also relates to nucleic acid sequences which hybridize to the coding sequences which comprise the single chain polypeptide comprising the heavy chain variable domain of antibody 14E1 and the light chain variable region domain of antibody 14E1. As used here, "stringent conditions" means any conditions in which hybridization will occur where there is at least about 95%, preferably 97%, nucleotide complementarity between the nucleic acids. See, e.g., Sambrook et al.

The polypeptides of the present invention can be administred to patients in need of therapy. To treat the disease, the compound, or mixture, can be formulated into pharmaceutical composition comprising a pharmaceutically acceptable carrier and other excipients as apparent to the skilled worker. See, e.g., *Remington's Phrmaceutical Sciences,* Eighteenth Edtion, Mack Publishing Company, 1990. Such composition can additionally contain effective amounts of other compounds, especially for treatment of cancer. The polypeptides can be administered intravenously, enterally, or parenterally. Generally, dosage ranges will be selected to achieve cytotoxic or cytostatic effects. The dosage will depend on the age, condition, sex, and extent of the disease in the patient. For example, dosages in the range of about 0.1 mg/kg can be administered, as single or multiple doses daily. A pharmaceutical composition can be used to treat various types of tumors, including carcinomas, gliomas, and melanomas.

The present invention can also be employed in vitro to purge a mixed population of cells having an antigen recognized by a polypeptide according to the present invention. For other aspects of the nucleic acids, polypeptides, antibody, etc., reference is made to standard textbooks of molecular biology, protein science, and immunology. See, e.g., Davis et a. (1986), Basic Methodes in Molecular Biology, Elsvir Sciences Publishing, Inc., New York; Hames et al. (1985), Nuceic Acid Hybridisation, IL Press, Molecular Cloning, Sambrook et al.; Current Protocols in Molecular Biology, Edited by F. M. Ausubel et al., John Wiley & Sons, inc; Current Protocols in Human Genetics, Edited by Nicholas C. Dracopoli et al., John Wily& sons, Inc.; Current Protocols in ProteinScience; Edited by John E. Coligan et al., John Wiley & Sons, Inc.; Current Protocols in Immunology; Edited by John E. Coligan et al, John Wiley & Sons Inc.

Without further elaboration, it is believed that one skilled in the art can, using the preciding description, utilize the present invention to its fullest extent. The preciding preferred specific embodiments are, therefore, to be construed as merely illustrative, and not limitative of the remainder of the disclosure in any way whatsoever.

The entire disclosure of all applications, patents and publications, cited above and below are herby incorporated by reference.

From the forgoing description, one skilled in the art can easily ascertain the essential characteristics of this invention, and whithout departing from the spirit and scope thereof, can make varios changes and modifications of the invention to adapt it to various usages and conditions.

BRIEF DESCRIPTION OF THE DRAWINGS

FIG. 7. Inhibition of the in vitro growth of NIH3T3 transfectants by recombinant toxins. DH-EΔ801-P cells expressing variant EGFRvIII, DH-EGFR-E cells expressing full-length EGFR, and DH-L2 control cells were incubated for 40 h with the indicated concentrations of the EGFR specific toxins scFv(14E1)-ETA, TGFα-ETA, or with the ErbB2 specific scFv(FRP5)-ETA as a control. The relative number of viable cells in comparison to PBS treated cells was determined using an enzymatic assay described in "background of examples". Each point represents the mean of a set of data determined in triplicates in three independent experiments.

FIGS. 9A–9H. A. Nucleotide sequence of VH 14E1(SEQ ID NO:1); B. Amino acid sequence of VH 14E1(SEQ ID NO:2); C. Nucleotide sequence of VL 14E1(SEQ ID NO:3); D. Amino acid sequence of VL 14E1 (VL #2)(SEQ ID NO:4); E. Nucleotide sequence of VL 14E1(SEQ ID NO:5); F. Amino acid sequence of VL 14E1 (VL #1)(SEQ ID NO: 6); G. Nucleotide sequence of scFv(14E1)(SEQ ID NO:7); and H. Amino acid sequence of scFv(14E1)(SEQ ID NO:8).

FIG. 10. Nucleotide and amino acid sequence of scFv (14E).

BACKGROUND OF EXAMPLES

Figure 1:
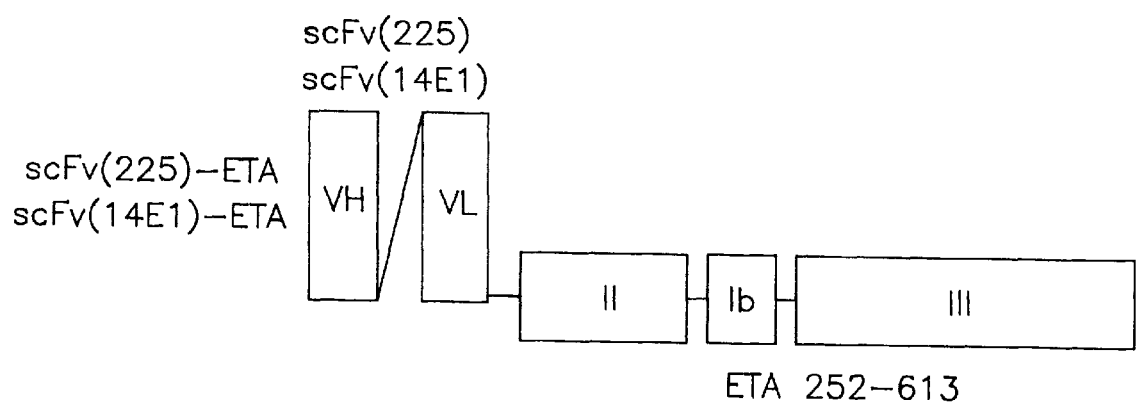
FIGS. 1A–1B Schematic representation of the recombinant single-chain antibody-toxins scFv(14E1)-ETA and scFv(225)-ETA, and the growth factor toxin TGFα-ETA. The bacterially expressed scFv-ETA proteins consist of the scFv domains of the monoclonal antibodies 225 or 14E1 containing the heavy ($V_H$) and light chain ($V_L$) variable domains fused to amino acids 252 to 613 of *Pseudomonas exotoxin* A (ETA) representing the translocation domain II, domain Ib, and domain III which mediates the ADP ribosylation of the eukaryotic elongation factor 2. TGFα-ETA contains amino acids 1 to 50 of human TGFα as an EGF receptor specific binding domain. Included in the molecules are the synthetic FLAG epitope and a cluster of 6 His residues at the N-terminus, and another cluster of 6 His residues N-terminal of ETA domain II facilitating the purification of the proteins via $Ni^{2+}$ affinity chromatography (not shown).
Figure 1:
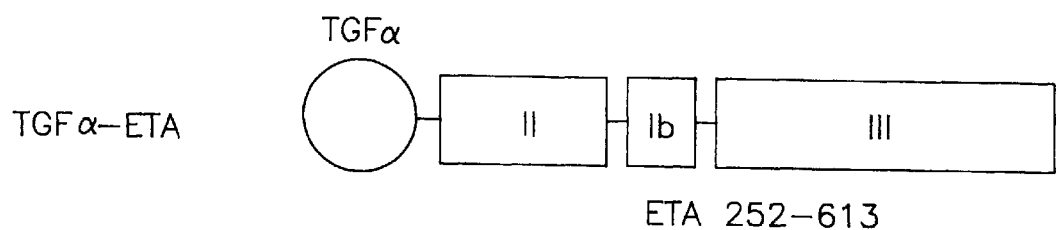

Cell Lines and Cell Culture. The SKBR3 and MDA-MB468 human breast tumor cell lines, the A431 human epidermoid tumor cell line and the NE1 mouse fibroblast cell line were maintained in Dulbecco's modified Eagle's medium containing 8% heat inactivated FCS. The generation of the stably transfected NIH3T3 cell lines DH-EGFR-E expressing human full-length EGFR cDNA, DH-EΔ801-P and DH-EA801-5 expressing EGFRvIII variant cDNA, and DH-L-2 control cells is described in detail by Hills et al., 1995 (Hills, D., Rowlinson-Busza, G., and Gullick, W. J. Specific targeting of a mutant, activated EGF receptor found in glioblastoma using a monoclonal antibody. Int. J. Cancer, 63: 537–543, 1995). The cells were cultured in Dulbecco's modified Eagle's medium supplemented with 10% heat inactivated fetal calf serum at 37° C. in a humidified atmosphere of air containing 5% $CO_2$.

Preparation of the 14E1 hybridoma. The hybridoma cell line 14E1 was prepared at Triton Diagnostics Inc. (Alameda, Calif.) by flusing splenocytes from mice immunized with A43 1 cells to the non-secreting mouse myeloma cell line SP2/0-Ag14 (both from ATCC, Rockville, Md.) according to the method of Köhler and Milstein (1975) (Nature 256:495–497 (1975)). Briefly, Balb/c mice were intraperitoneally immunized with $10^7$ A431 cells emulsified in an equal volume of RIBI adjuvant (RIBI Immunochem Research Inc., Hamilton, Mont.) and boosted every two weeks. Sera were collected and tested biweekly by ELISA for reactivity against A431 cell lysate and the extracellular portion of the EGF receptor purified from A431 cell conditioned media (Science, 224: 294–297 (1984)). Mice with positive titers were intravenously boosted with antigen in PBS and sacrificed four days later. A 4:1 ratio of splenocytes to myeloma cells were fused using a 50% polyethylene glycol solution, and plated in 96 wells at a density of $2.5 \times 10^5$ splenocytes per well in RPMI supplemented with 0.1 mM hypoxanthine and 5.8 μM azaserine to select for hybrids. Supernatants were screened by ELISA for EGF receptor specificity; positive clones were isolated and put through two additional rounds of subcloning. Antibodies were raised in ascites and purified on protein G-agarose. Several EGF receptor specific clones were isolated; one of these, 14E1 (IgG), which recognizes the extracellular portion of the EGF receptor, was shown to compete with EGF and TGFα for receptor binding in radioligand binding assays (data not shown).

Construction of scFv(14E1) and scFv(14E1)-ETA. 14E1 hybridoma cell mRNA was isolated using a Quick Prep RNA purification kit (Pharmacia Biotech, Brussels, Belgium). First strand cDNA synthesis was carried out according to the manufacturer's recommendations using a cDNA synthesis kit (Stratagene) with 100 ng mRNA and random primers. For amplification of the heavy (VH) and light chain (VL) variable domains the first strand cDNA served as a template in a PCR as described (Wels el al., 1992). For amplification of the VH domain, 50 pmol each of the oligonucleotides 5'-AGGTSMARCTGCAG-SAGTCWGG-3' (SEQ ID NO:9)and 5'-TGAGG-AGACGGTGACCGTGGTCCCTTGGCCCC-3' (SEQ ID NO:10) were used, for amplification of the VL kappa domain, 50 pmol each of the oligonucleotides 5'-GCGACCTTGCACGCGTAGACATTGAGCTCACCC-AGTCTCCA-3' (SEQ ID NO:11), and 5'-CG-CTACAATAGCGGCCGCTACCGTCCGTTTGATTTCC-AGCTTGGTGCC-3' (SEQ ID NO:12) or 5'-CGCTACATTAGCGGCCGCTACCGTCCGTTTCAG-CTCCAGCTTGGTCCC-3' (SEQ ID NO:13) were used (M=A+C, R=A+G, S=C+G, W=A+T, Y=C+T, K=G+T). Subsequently, the VH and VL PCR products were reamplified using 50 pmol each of the oligonucleotide primers 5'-TGAGGAGACGGTGACCGTGGTCCCTTGGCCCCA-G-3' (SEQ ID NO:14) and 5'-ATTATAAGCTTCAGGT-SMARCTGCAGSAGTCWGG-3' (SEQ ID NO:15) (VH), or 5'-TTAGATCTCTAGAAKCTCGAGYTTKGTSC-3' (SEQ ID NO:16) and 5'-GACATTCAGCTGA-CCCAGWCTSC-3' (SEQ ID NO:17) (VL), respectively. PCR products were digested with HindIII and BstEII (VH), or with PvuII and XbaI (VL). Mab 14E1 VH cDNA was inserted into HindIII/BstEII digested plasmid pWW152 (Wels et al., 1992) which contains a sequence encoding the 15 amino acid linker $(GGGGS)_3$. Subsequently, the 14E1 VL fragment was inserted 3' of the VH and linker sequences, resulting in the scFv(14E1I) encoding plasmid pWW152-14E1. For bacterial expression the scFv(14E1) sequence was isolated as a HindIII/XbaI fragment from pWW152 and inserted into HindIII/XbaI digested plasmid pSW50 (Wels et al., 1995). For the construction of the scFv(14E1)-ETA toxin fusion the scFv(14E1) fragment was inserted into HindIII/XbaI digested plasmid pSW202 containing a truncated Pseudomonas ETA gene which lacks the original cell binding domain Ia of the toxin (Wels el al., 1995). The resulting plasmids pSW50-14E1 and pSW202-14E1 encode, respectively, the scFv(14E1) and scFv(14E1)-ETA proteins, fused at the N-terminus to the ompA signal sequence, the synthetic FLAG epitope, and a cluster of 6 His residues, under the control of an IPTG inducible tac promoter.

Expression and purification of scFv and scFv-ETA fusion proteins. Single colonies of E. coli CC118 carrying plasmids pSW50-14E1 or pSW50–225 (Wels et al., 1995) for the expression of EGF receptor specific scFv proteins, or plasmids pSW202–14E1 or pSW202–225 (Wels et al., 1995) for the expression of scFv-ETA fusion proteins were grown overnight at 37° C. in LB medium supplemented with 0.6% glucose and 100 µg/ml ampicillin. E. coli CC118 carrying plasmid pSW202-TGFα (Schmidt and Wels, 1996) were used for the expression of TGFα-ETA, a recombinant growth factor toxin which consists of amino acids 1 to 50 of human TGFα fused to truncated Pseudomonas ETA. The cultures were diluted 30-fold in the same medium, grown at 37° C. to an $OD_{550}$ of 0.7 and induced with 0.1 mM IPTG for 1 h at room temperature. Cells were harvested by centrifugation at 10,000 g for 10 min at 4° C., the cell pellet from 1l of culture was resuspended in 15 ml PBS containing 6M guanidine hydrochloride, and lysed by sonication. Following incubation at room temperature for 30 min the lysate was clarified by centrifugation at 30,000 g for 30 min at 4° C. The supernatant was diluted to 3M guanidine hydrochloride with PBS and recombinant proteins were purified via binding to $Ni^{2+}$-saturated chelating sepharose (Pharmacia Biotech). Specifically bound proteins were eluted with 3M guanidine hydrochloride, 250 mM imidazole in PBS. Fractions containing recombinant fusion proteins were pooled and dialysed twice against PBS, 400 mM L-arginine and PBS, respectively. Typical yield of purified proteins was 1 mg per 1 of original bacterial culture with a purity of approximately 70% determined by SDS-PAGE and Coomassie brilliant blue staining.

ScFv-ETA binding assay. The binding of scFv-ETA proteins to the EGF receptor was measured by ELISA as described (Schmidt el al., 1996). 96 well microtiter plates coated with recombinant protein comprising the extracellular domain of the human EGF receptor were blocked with 3% BSA in TBS (10 mM Tris-HCl, pH 7.5, 150 mM NaCl). 50 µl of scFv(225)-ETA or scFv(14E1)-ETA at concentrations ranging from 0.03 nM to 1 µM were added to the wells and the plates were incubated for 1 h at 37° C. Unbound protein was removed, the wells were washed and incubated with 100 µl of rabbit anti-exotoxin A serum for 1 h at 37° C. followed by incubation with 100 µl of goat anti-rabbit IgG coupled to alkaline phosphatase (Sigma, St. Louis, Mo.). Specifically bound scFv-ETA proteins were detected by incubation with a solution of 1M Tris-HCl, pH 8.0, 1 mg/ml p-nitrophenylphosphate disodium (Sigma) for 30 min at room temperature, then the absorbance at 405 mn was measured.

Cell viability assay. The cell killing activity of ETA fusion proteins was measured basically as described (Wels et al., 1992). The cells were seeded in 96 well plates at a density of $1 \times 10^4$ cells/well in normal growth medium. Various concentrations of ETA fusion proteins were added to triplicate samples and the cells were incubated for 40 h. 10 µl of 10 mg/ml MT (3-(4,5-dimethylthiazole-2-yl)-2,5 diphenyltetrazolium bromide) (Sigma) in PBS were added to each well and the cells were incubated for another 3 h. Cells were Lysed by the addition of 90 µl of 20% SDS in 50% dimethyl formamide, pH 4.7. After solubilization of the formazan product, the OD at 590 nm of each sample was determined in a microplate reader (Dynatech) as a measure of the relative amount of viable cells in comparison to cells grown without the addition of recombinant proteins.

Competition experiments. Competition of TGFα-ETA binding by scFv proteins was analyzed in a cell viability assay as described above. SKBR3, MDA-MB468, and A43 1 cells were incubated with 100 ng/ml of TGFα-ETA alone or in the presence of 10 µg/ml scFv(14E1) or scFv(225) as competitors. After 40 h cell viability was determined. Competition of scFv-ETA binding by the Mab 225 was analyzed using A43 1 cells. The cells were incubated with 100 ng/ml of scFv(225)-ETA or scFv(14E1)-ETA with or without the addition of a 100-fold molar excess of the EGF receptor specific Mab 225 as a competitor. After 40 h the relative number of viable cells was determined as described above.

Time course of scFv-ETA cell killing. A43 1 cells were seeded in 96 well plates at a density of $1 \times 10^4$ cells per well. After attachment of the cells the medium was removed and the cells were treated for various time intervals with 100 ng/ml of scFv-ETA proteins in normal growth medium. The medium was removed, cells were washed twice with PBS, and grown for another 40 h in normal growth medium. Cell viability was measured as described above.

Receptor Activation Assay. A431 human epidermoid carcinoma cells and NE1 mouse fibroblasts expressing a human EGF receptor cDNA (Beerli el al., 1994) were grown for 16 h in DMEM supplemented with 0.5% FCS. A431 cells were treated with purified recombinant TGFα-ETA at a concentration of 1 µg/ml with or without the addition of 50 µg/ml scFv(14E1)-ETA or scFv(225)-ETA as competitors. Control cells were treated with PBS or 20 ng/ml EGF. NE 1 cells were treated with EGF at a concentration of 10 ng/ml alone or in the presence of 20 µg/ml scFv(14E1)-ETA or scFv (225)-ETA. Control cells were incubated with PBS or with scFv-ETA proteins in the absence of EGF. Following incubation at 37° C. for 10 min the cells were lysed in a buffer containing 50 mM Tris-HCl, pH 8.0, 5 mM EGTA, 150 mM NaCl, 1 mM PMSF, 2 mM $NaVO_4$, 50 mM NaF, 50 mM Na-Molybdate, 1% Triton X-100, 0.5% desoxycholate, 0.1% SDS. Extracts were clarified by centrifugation at 10,000 g for 10 min at 4° C. Cleared cell lysates containing 15 µg each of total proteins were applied on a 7.5% SDS-PAGE. After electrophoresis proteins were blotted on a PVDF membrane (Millipore) and phosphotyrosine containing proteins were detected by incubation of the membrane with an anti-phosphotyrosine Mab (Santa Cruz Biotechnology, Santa Cruz, Calif., USA), followed by incubation with an anti-mouse horse radish peroxidase coupled antibody and chemiluminescent detection with the ECL kit (Amersham).

EXAMPLES

Example 1

Construction and bacterial expression of scFv(14E1)-ETA. The 14E1 hybridoma producing a novel anti-EGF receptor monoclonal antibody (IgG. κ) was derived by immunization of mice with human A43 1 epidermoid carcinoma cells and fusion of splenocytes following standard protocols. cDNAs encoding the heavy (VH) and light chain (VL) variable domains of the 14E1 Mab were derived from 14E1 hybridoma cell mRNA by reverse transcription and amplification using PCR. A single chain Fv gene was created by connecting VH and VL sequences via a synthetic linker encoding the 15 amino acids $(GGGGS)_3$, and the scFv gene was fused to sequences encoding a truncated form of *Pseudomonas aeruginosa exotoxin A* (ETA) in the pSW202 vector as described (Wels et al., 1992 a; Wels et al., 1995). The resulting expression plasmid pSW202-14El encodes under the control of an IPTG inducible tac promoter a fusion protein consisting of the *E. coli* ompA signal peptide at the N-terminus, followed by the synthetic FLAG epitope, 6 His residues, the scFv(14E1), 6 His residues, and ETA amino acids 252 to 613. The structure of the scFv(14E1)-ETA gene product is schematically shown in FIG. 1A. The ETA portion of the molecule lacks the native cell binding domain Ia of the toxin but contains the translocation domain II which is required for processing of the toxin and release into the cytoplasm after internalization into target cells via the endosomal route, and the enzymatic domain III which catalyzes the ADP-ribosylation of eukaryotic elongation factor EF-2 thereby arresting cellular protein synthesis (Ogata et al., 1992).

The scFv(14E1)-ETA antibody-toxin and two previously described recombinant toxins with specificity for the EGF receptor, scFv(225)-ETA (Wels et al., 1995) and TGFα-ETA (Schmidt et al., 1996) were expressed in *E. coli* strain CC118. Total bacterial lysates were prepared in 6M guanidine hydrochloride, the lysates were diluted to 3M guanidine hydrochloride and the recombinant toxins were purified by binding to $Ni^{+2}$-saturated chelating sepharose and elution with 250 mM imidazole. Fractions containing the recombinant scFv-ETA proteins were pooled, imidazole and denaturant were removed by dialysis and the proteins were concentrated by ultrafiltration. SDS-PAGE analysis of the purified material revealed a purity of greater than 70% after a single round of $Ni^{2+}$ affinity purification (data not shown). Likewise, scFv(14E1) and scFv(225) proteins which lack the C-terminal toxin domain were expressed and purified (data not shown). The yield of purified recombinant proteins from 1 1 of bacterial culture was typically 1, 0.5, and 2 mg of scFv-ETA, TGFα-ETA, and scFv proteins, respectively.

Example 2

Binding properties of scFv(14E1)-ETA. ELISA experiments were performed to determine the binding of scFv (14E1) to the EGF receptor. ScFv(14E1)-ETA at concentrations ranging from 0.03 nM to 1 μM was added to the wells of 96 well plates coated with purified recombinant extracellular domain of the EGF receptor, the plates were incubated at 37° C. for 1 h and specifically bound protein was determined. The similar scFv(225)-ETA molecule was used as a control. The results are shown in FIG. 2A Both proteins, scFv(14E1)-ETA and scFv(225)-ETA specifically bound to the extracellular portion of the EGF receptor in a saturable fashion. The apparent binding affinity of the scFv(14E1-ETA to EGF receptor, calculated as the half-maximal saturation value, was 1 nM. The apparent binding affinity of scFv(225)-ETA to EGF receptor was much lower with a half maximal saturation value of 9 nM. Previously an apparent affinity of 12 nM was determined for scFv(225)-ETA in a similar ELISA experiment with immobilized A431 cells as antigen (Wels et al., 1995).

The parental Mab 225 as well as recombinant scFv(225) molecules derived thereof compete the binding of EGF to the EGF receptor thereby inhibiting receptor activation (Fan et al., 1993; Beerli et al., 1994; Wels et al., 1995). In order to test whether the scFv(14E1) domain can also block the binding of EGF, competition experiments were performed. NEI murine fibroblasts expressing human EGF receptor cDNA (Beerli el al., 1994) were grown in low serum for 16 hr and then treated for 10 min at 37° C. with 10 ng/ml EGF with or without the addition of 20 μg/ml of scFv(14E1)-ETA or scFv(225)-ETA as competitors. Control cells were treated with PBS or scFv-ETA proteins in the absence of EGF. Equal amounts of cell lysates were assayed for their phosphotyrosine content by SDS-PAGE and subsequent immunoblotting with a specific anti-phosphotyrosine monoclonal antibody, followed by incubation with an anti-mouse horseradish peroxidase labeled antibody and chemiluminescent detection. The results are not shown. Treatment of cells with EGF led to a strong increase in the phosphotyrosine content of a protein corresponding in size with the 170 kDa EGF receptor, which was confirmed by reprobing the filter with an anti-EGF receptor serum (data not shown). This EGF-induced activation of the receptor was blocked to a great extent by scFv(225)-ETA whereas scFv(14E1)-ETA completely abolished receptor activation. PBS and ScFv-ETA proteins alone had no effect on the phosphotyrosine content of the receptor. The results show that the recombinant scFv(l4E1)-ETA similar to scFv(225)-ETA is able to block EGF-induced receptor activation, but is much more potent than the latter at identical concentrations.

Example 3

Figure 3:
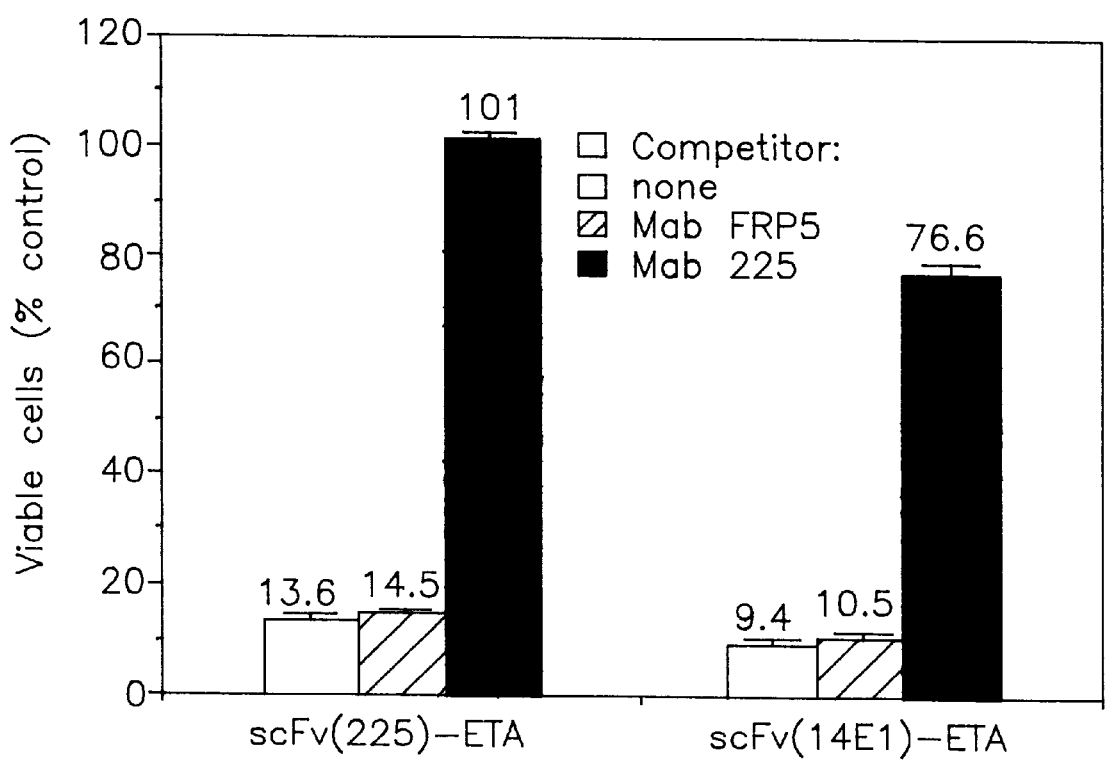
FIG. 3. Competition of the cytotoxic activity of scFv(225)-ETA and scFv(14E1)-ETA by the monoclonal antibody 225. A431 human squamous cell carcinoma cells were incubated for 40 h with 100 ng/ml scFv(225)-ETA (left) or scFv(14E1)-ETA (right) without the addition of competitor or in the presence of a 100-fold molar excess of the EGF receptor specific Mab 225 as a specific competitor, or the isotype-matched control antibody FRP5 as indicated. The relative number of viable cells was determined using an enzymatic assay as described in "background of examples". Each point represents the mean of a set of data determined in triplicate.

In vitro cytotoxicic activity and specificity of scFv(14E1) ETA. Both antibody-toxins, scFv(14E1)-ETA and scFv (225)-ETA inhibit the activation of EGF receptor by EGF. In order to analyze the potential of Mab 225 to interfere with scFv(14E1)-ETA binding, cell killing experiments were carried out. The cytotoxic activity of scFv(14E1)-ETA was tested on A431 cells using an enzymatic assay (Wels et al., 1992 a). The cells were incubated for 40 h with 100 ng/ml (1.5 nM) of scFv(14E1)-ETA or scFv(225)-ETA in the absence or presence of a 100-fold molar excess of Mab 225 and cell viability was measured in comparison to PBS treated cells. The isotype-matched ErbB-2 specific Mab FRP5 (Harwerth et al., 1992) was included as a control. The results are shown in FIG. 3. At the concentration used, both antibody-toxins displayed similar cell killing activity; approximately 90% and 86% of the cells were killed by scFv(14E1)-ETA (FIG. 3, right panel) and scFv(225)-ETA (FIG. 3, left panel), respectively. In the presence of an excess of the specific competitor, Mab 225, the cytotoxic activity was reduced in both cases. No cell killing was observed in the case of scFv(225)-ETA; approximately 33% of the cells were killed in the case of scFv(14E1). An excess of the non-specific Mab FRP5 had no effect on the cytotoxic activity of the scFv-ETA proteins. The results show that the cytotoxic activity of scFv(14E1)-ETA is specifically targeted to the EGF receptor, since cell killing can be competed by the EGF receptor specific Mab 225.

Example 4

In vitro cell killing activity of recombinant toxins specific for the EGF receptor. Since scFv(14E1)-ETA displays a significantly higher affinity for the EGF receptor, cell killing experiments were performed to investigate whether the increased affinity results in enhanced cytotoxicity towards EGF receptor expressing cells. In addition, TGFα-ETA was included in the experiment, a recombinant fusion toxin which employs the natural EGF receptor ligand TGFα as a cell targeting domain (Schmidt et al., 1996). The structure of TGFα-ETA which is schematically shown in FIG. 1A, is very similar to that of the TGFα-PE40 molecule previously characterized by others (Siegall et al., 1989). The in vitro toxicity of the scFv(14E1)-ETA, the scFv(225)-ETA, and the TGFα-ETA proteins was tested on three human tumor cell lines. The A431 epidermoid and the MDA-MB468 breast carcinoma cells express between 1 and 2 million EGF receptors per cell, whereas the SKBR3 breast carcinoma cells express approximately 50-fold lower EGF receptor levels on their surface (Wels et al., 1995).

Figure 4A:
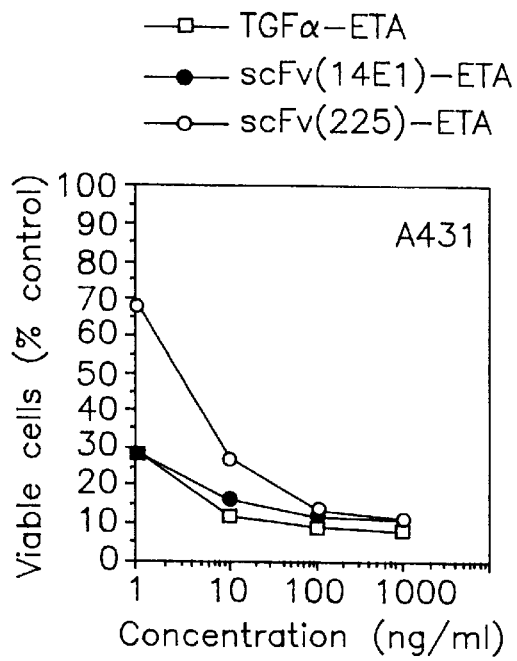
FIG. 4. In vitro cell killing activity of scFv-ETA proteins and TGFα-ETA. A431 human squamous cell carcinoma cells (upper left panel), and MDA-MB468 (upper right panel) and SKBR3 (lower left panel) human breast carcinoma cells were incubated for 40 h with the indicated concentrations of scFv(225)-ETA (open circles), scFv (14E1)-ETA (closed circles), or TGFα-ETA (open boxes). In addition SKBR3 cells were treated with the ErbB-2 specific scFv(FRP5)-ETA (closed triangles). The relative number of viable cells was determined as described in FIG. 3 and "background of examples". Each point represents the mean of a set of data determined in triplicate in 3 independent experiments.
Figure 4B:
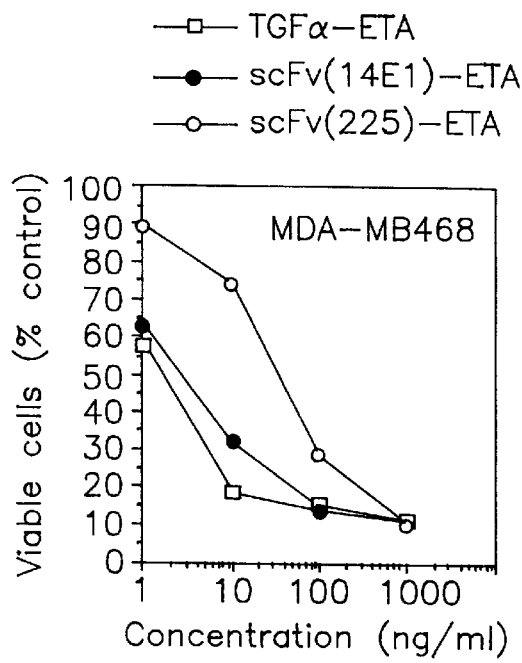
Figure 4C:
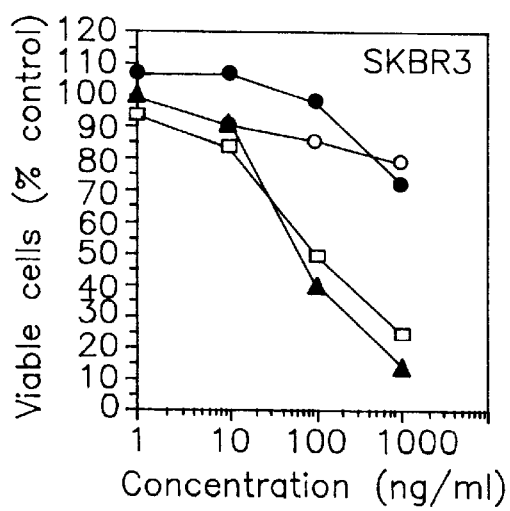

The cells were incubated for 40 h with various concentrations of the EGF receptor specific scFv-ETA and TGFα-ETA proteins. As a control, the SKBR3 cells which overexpress ErbB-2 were also treated with the ErbB-2 specific antibody-toxin scFv(FRP5)-ETA (Wels et al., 1992 a). The relative number of viable cells in comparison to untreated controls was determined with an enzymatic assay (Wels et al., 1992 a). The results are shown in FIG. 4. A43 1 cells were very sensitive to the toxins with scFv(14E1)-ETA and TGFα-ETA showing similar activity ($IC_{50}$ below 1 ng/ml) and scFv(225)-ETA being less potent at lower toxin concentrations ($IC_{50}$ 3 ng/ml) (FIG. 4, upper left panel). Very similar results were obtained with MDA-MB468 cells (FIG. 4, upper right panel). TGFα-ETA and scFv(14E1)-ETA displayed similar cell killing activity with $IC_{50}$ values of approximately 2 and 3 ng/ml, respectively. ScFv(225)-ETA was also cytotoxic for MDA-MB468 cells in a dose dependent fashion, but with a much higher $IC_{50}$ value of approximately 40 ng/ml. The EGF receptor specific antibody-toxins scFv(14E1)-ETA and scFv(225)-ETA at concentrations of up to 1 µg/ml did not display significant cell killing activity on SKBR3 cells expressing high amounts of ErbB-2 but only moderate levels of the EGF receptor (FIG. 4, lower panel). In striking contrast, the recombinant growth factor toxin TGFα-ETA was cytotoxic for SKBR3 cells at relatively low concentrations with an $IC_{50}$ value of approximately 90 ng/ml comparing to an $IC_{50}$ of approximately 50 ng/ml for the ErbB-2 specific antibody-toxin scFv(FRP5)-ETA. Similar results were also obtained with T47D human breast tumor cells which like SKBR3 cells express only low levels of the EGF receptor. T47D cells were sensitive to TGFα-ETA ($IC_{50}$ of 105 ng/W) (Schmidt and Wels, 1996) but highly resistant to scFv(14E1)-ETA and scFv(225)-ETA ($IC_{50}$>1 µg/ml; data not shown). The results show that scFv(14E1)-ETA is highly cytotoxic for tumor cells overexpressing the EGF receptor. Its activity is comparable to that of TGFα-ETA, but much more potent than that of scFv(225)-ETA. Importantly, both antibody-toxins in contrast to the growth factor toxin are highly selective for EGF receptor overexpressing cells.

Figure 5:
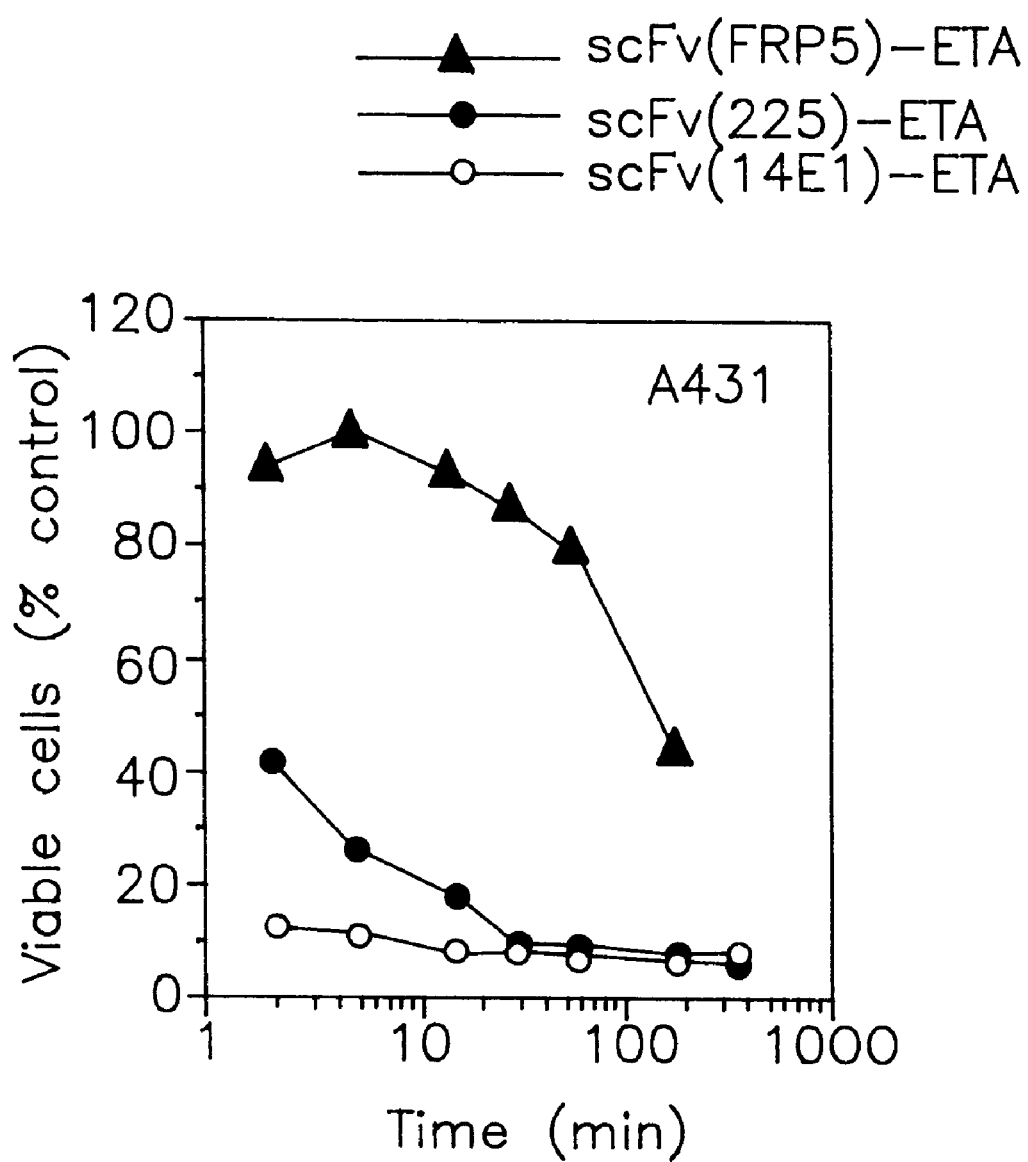
FIG. 5. Kinetics of scFv-ETA cell killing on A431 cells. The cells were incubated with 100 ng/ml of scFv(225)-ETA (closed circles), scFv(14E1)-ETA (open circles), or scFv (FRP5)-ETA (closed triangles) for various time intervals as indicated. After treatment the toxins were removed and the cells were incubated for another 40 h in normal growth medium. The relative number of viable cells was determined as described in FIG. 3 and "background of examples". Each point represents the mean of a set of data determined in triplicate.

In order to analyze the kinetics of scFv-ETA binding to tumor cells and scFv-ETA-mediated cell killing, a time course experiment was carried out. A43 1 cells were treated for defined time intervals with 100 ng/ml each of scFv (14E1)-ETA and scFv(225)-ETA, respectively. Control cells were treated with the ErbB-2 specific scFv(FRP5)-ETA protein. Unbound scFv-ETA proteins were removed and the cells were incubated in normal growth medium for another 40 h. The relative number of viable cells was determined as described above. The results are shown in FIG. 5. Potent cell killing was achieved after short incubation of the cells with the EGF receptor specific scFv-ETA proteins. While maximal cell killing by scFv(14E1)-ETA was already observed after incubation for 2 min, a similar effect was achieved only after incubation for 30 min with scFv(225)-ETA. In contrast, A43 1 cells which express low levels of ErbB-2 had to be treated with the ErbB-2 specific scFv(FRP5)-ETA for 100 min to achieve significant cell killing. Our data show that A431 cell killing mediated by EGF receptor specific scFv-toxins follows different kinetics than cell killing by the ErbB-2 specific toxin. This might not only reflect the approximately 50-fold difference in EGF receptor and ErbB-2 expression which could allow a more rapid binding of amounts of anti-EGF receptor toxins sufficient for cell killing, but could also be due to differences in the internalization rates and intracellular pathways of EGF receptor and ErbB-2. The much faster cell killing by scFv(14E1)-ETA in comparsion to scFv(225)-ETA is likely due to the higher affinity of the former. Differences in the internalization and the intracellular routing of toxin-receptor complexes seem unlikely since both scFvs bind to an identical or very similar epitope and do not induce receptor activaton upon binding.

Example 5

Inhibition of TGFα-ETA binding by scFv proteins. Many human tumor cells which overexpress EGF receptors also synthesize increased amounts of TGFα, which is transported to the cell surface and activates EGF receptors in an autocrine fashion (Derynck et al., 1987; Van de Vijver et al., 1991). This in turn can lead to an increased growth response of the tumor cells. The antagonistic Mab 225 displays growth inhibitory activity on tumor cells in vitro in the absence of active complement or immune effector cells, suggesting that the antitumoral activity of the antibody is mainly due to its ability to block EGF receptor activation and to interrupt autocrine stimulation by TGFα (Ennis et al., 1989). The very rapid cell killing effect observed after treatment of tumor cells with scFv(14E1)-ETA and scFv (225)-ETA suggests that the inhibition of in vitro tumor cell growth by these proteins is mainly due to their cytotoxic activity. Nevertheless, the ability to interfere with TGFα binding to the EGF receptor and TGFα-induced receptor activation might be an additional advantage on autocrine stimulated tumor cells. In order to test the capacity of the scFv domains themselves to block TGFα binding, competition experiments with scFv(14E1) and scFv(225) proteins lacking the cytotoxic ETA domain were performed.

A431 cells were treated for 10 min at 37° C. with 500 ng/ml of TGFα-ETA with or without the addition of 50 µg/ml of scFv(14E1) or scFv(225) as competitors. Control cells were treated with PBS or 20 ng/ml EGF. Equal amounts of cell lysates were assayed for their phosphotyrosine content by SDS-PAGE and subsequent immunoblotting with a specific antiphosphotyrosine monoclonal antibody, followed by incubation with an anti-mouse horseradish peroxidase labeled antibody and chemiluminescent detection. The results are not shown. Treatment of cells with TGFα-ETA led to a strong increase in the phosphotyrosine content of the EGF receptor comparable to treatment with EGF. No TGFα-ETA-induced activation of the receptor was observed with scFv(14E1) as a competitor, whereas scFv(225), while also active as a competitor, was unable to completely abolish EGF receptor activation. PBS had no effect on the phosphotyrosine content of the receptor. Similar to the results obtained with scFv-ETA proteins the data show that the recombinant scFv domains of Mab 14E1 and 225 alone are able to block ligand-induced receptor activation, but that scFv(14E1) is much more potent than scFv(225).

Figure 6A:
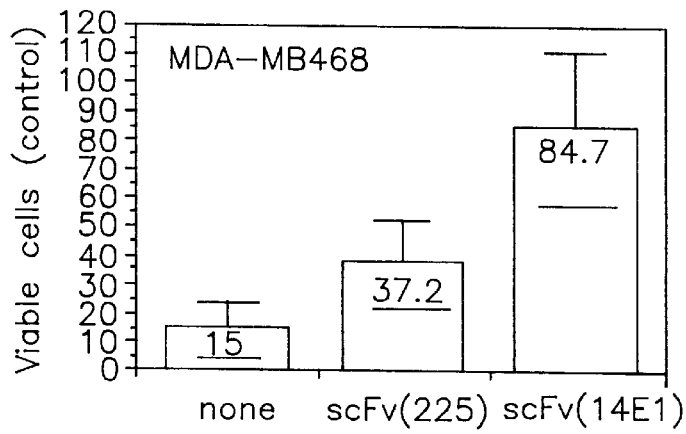
FIG. 6. Competition of the cytotoxic activity of TGFα-ETA by scFv(225) and scFv(14E1). MDA-MB468 (upper panel), A431 (middle panel), and SKBR3 cells (lower panel) were incubated for 40 h with 100 ng/ml TGFα-ETA in the-absence of competitor, or in the presence of 10 μg/ml of scFv(225) or scFv(14E1) as indicated. The relative number of viable cells was determined as described in FIG. 3 and "background of examples". Each point was determined in triplicate. The standard deviation is represented by error bars.
Figure 6B:
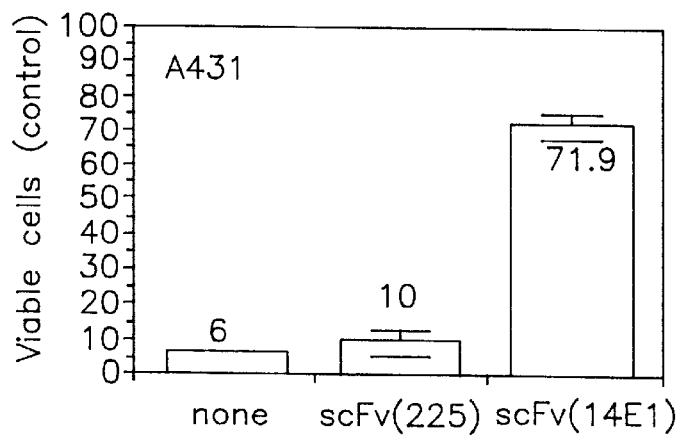
Figure 6C:
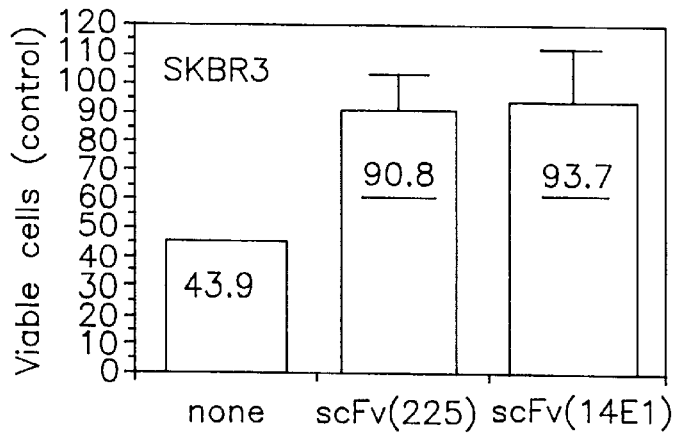
Figures 8A, 8B:
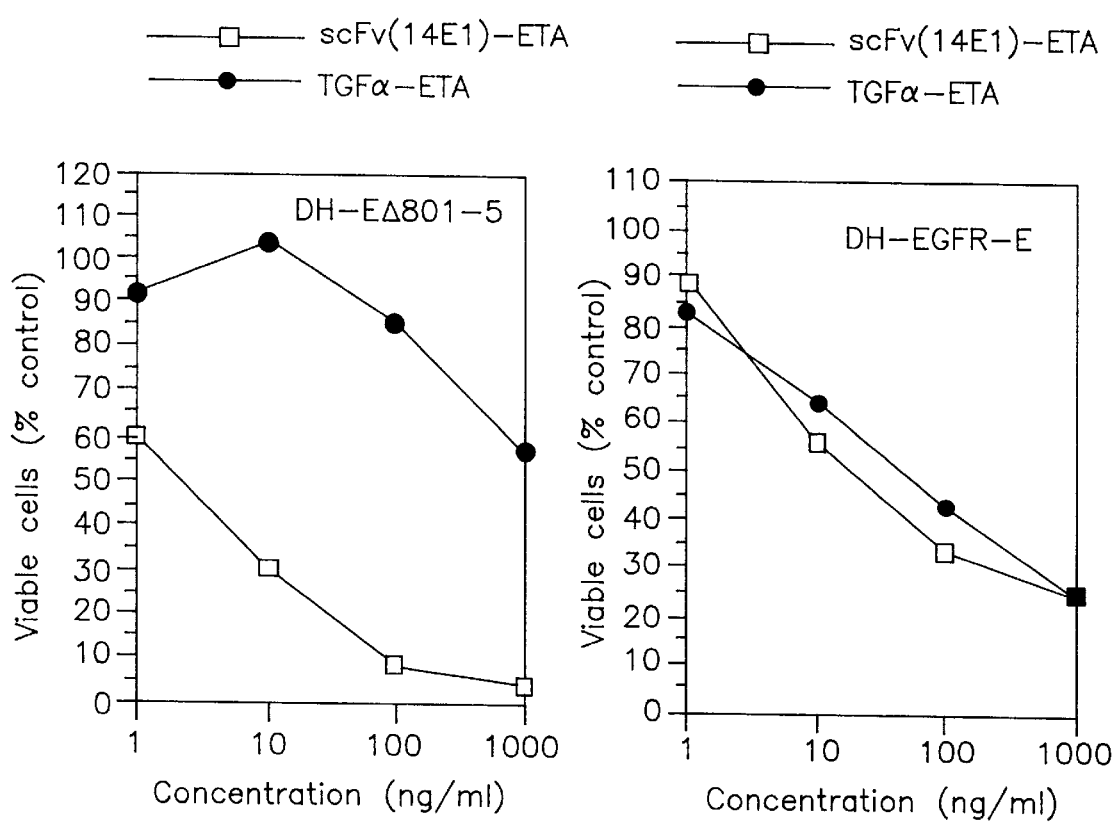
FIG. 8 Inhibition of the in vitro growth of DH-EΔ801-5 cells by recombinant toxins. DH-EΔ801-5 cells were incubated for 40 h with the indicated concentrations of the EGFR specific toxins scFv(14E1)-ETA or TGFα-ETA and the relative number of viable cells was determined as described in the legend of FIG. 2. For comparison a corresponding experiment with DH-EGFR-E cells is shown (data are from FIG. 7).

To analyze the competition of TGFα binding by scFv (14E1) and scFv(225) in more detail, an experiment was carried out to block the cytotoxic effect of TGFα-ETA on several human tumor cell lines by addition of the scFv proteins. MDA-MB468, A43 1, and SKBR3 cells were incubated for 40 h with 100 ng/ml of TGFα-ETA with or without the addition of 10 µg/ml of scFv(14E1) or scFv (225), and cell viability was measured in comparison to PBS treated cells as described above. The results are shown in FIG. 7. Both scFv proteins potently inhibited TGFα-ETA cytotoxicity on SKBR3 cells expressing moderate levels of the EGF receptor. Without competitor, approximately 56% of the cells were killed whereas in the presence of either scFv protein cell killing was reduced to less than 10% (FIG. 7, lower panel). On A431 cells overexpressing the EGF receptor, cell killing was almost complete after incubation with TGFα-ETA (94% cell killing) (FIG. 6, middle panel). Addition of an excess of scFv(225) hardly influenced the cytotoxic effect of TGFα-ETA resulting in approximately 90% cell killing. In contrast, scFv(14E1) was very potent in blocking the cytotoxic activity of TGFα-ETA on A43 1 cells reducing cell killing to approximately 28%. Similar results were obtained MDA-MB468 cells (FIG. 6, upper panel). TGFα-ETA treatment alone resulted in approximately 85% cell killing whereas the addition of scFv(225) or scFv(14E1) reduced the cell killing by TGFα-ETA to approximately 63% and 15%, respectively. The results show that scFv (14E1) is a much more potent competitor of TGFα binding than scFv(225), and that scFv(14E1) can protect cells from attack by TGFα-ETA over a prolonged period of time.

Example 6

Monoclonal Antibody 14E1 Binds to Full-Length and Variant EGFR DH-EGFR-E and DH-EΔ801-P are NIH3T3 cell lines stably transfected with human full-length and variant EGFR cDNAs, respectively (Hills, D., Rowlinson-Busza, G., and Gullick, W. J. Specific targeting of a mutant, activated EGF receptor found in glioblastoma using a monoclonal antibody. Int. J. Cancer, 63: 537–543, 1995). The phosphotyrosine content of EGFR proteins in DH-EGFR-E and DH-EA801-P cells was determined. The cells were grown in low serum for 16 hr and the treated for 10 min at 37° C. with 20 ng/ml EGF or with PBS. Equal amounts of cell lysates were assayed for their phosphotyrosine content by SDS-PAGE and subsequent immunoblotting with a specific antiphosphotyrosine monoclonal antibody, followed by incubation with an anti-mouse horseradish peroxidase labeled antibody and chemiluminescent detection. The results are not shown. In DH-EΔ801-P cells the variant EGFRvIII displayed high constitutive phosphotyrosine levels which were very similar in the absence or in the presence of EGF. In DH-EGFR-E cells full-length EGFR did not contain measurable amounts of phosphotyrosine in the absence of EGF, but was strongly phosphorylated on tyrosine residues upon EGF treatment. The murine Mab 14E1 binds to the extracellular domain of human EGFR. The ability of Mab 14E1 to recognize EGFRvIII which lacks amino acids 6 to 273 of the extracellular domain was tested in immunoblot experiments. Equal amounts of cell lysates from DH-EGFR-E and DH-EΔ801 -P cells, or from DH-L-2 control cells transfected with an empty vector construct (Hills, D., Rowlinson-Busza, G., and Gullick, W. J. Specific targeting of a mutant, activated EGF receptor found in glioblastoma using a monoclonal antibody. Int. J. Cancer, 63: 537–543, 1995) were separated by SDS-PAGE, electroblotted onto PDVF membranes, and analyzed with Mab 14E1 (data not shown). As a control a similar experiment was performed using Mab DH8.3 which is specific for EGFRvIII (Hills, D., Rowlinson-Busza, G., and Gullick, W. J. Specific targeting of a mutant, activated EGF receptor found in glioblastoma using a monoclonal antibody. Int. J. Cancer, 63: 537–543, 1995) (data not shown). As expected, Mab DH8.3 recognized the EGFRvIII protein expressed by DH-EA801-P cells but did not bind to proteins from DH-EGFR-E and DH-L-2 cells. In contrast, under non-reducing conditions Mab 14E1 detected both, full-length human EGFR and EGFRvIII expressed by DH-EGFR-E and DH-EΔ801-P cells, respectively, but did not bind to control proteins. When cellular lysates were applied to the gel under reducing conditions, Mab 14E1 failed to detect the EGFR proteins (data not shown).

Example 7

EGFRvIII Expressing Cells are Differentially Sensitive to the Antibody-Toxin scFv(14E1)-ETA and the Growth Factor Toxin TGFα-ETA. Mab 14E1 and recombinant single-chain Fv derivatives of Mab 14E1 compete the binding of the natural EGFR ligands EGF and TGFα to the receptor, suggesting that the antibody binds to an EGFR epitope very close to the binding site of the growth factors.

Figure 2:
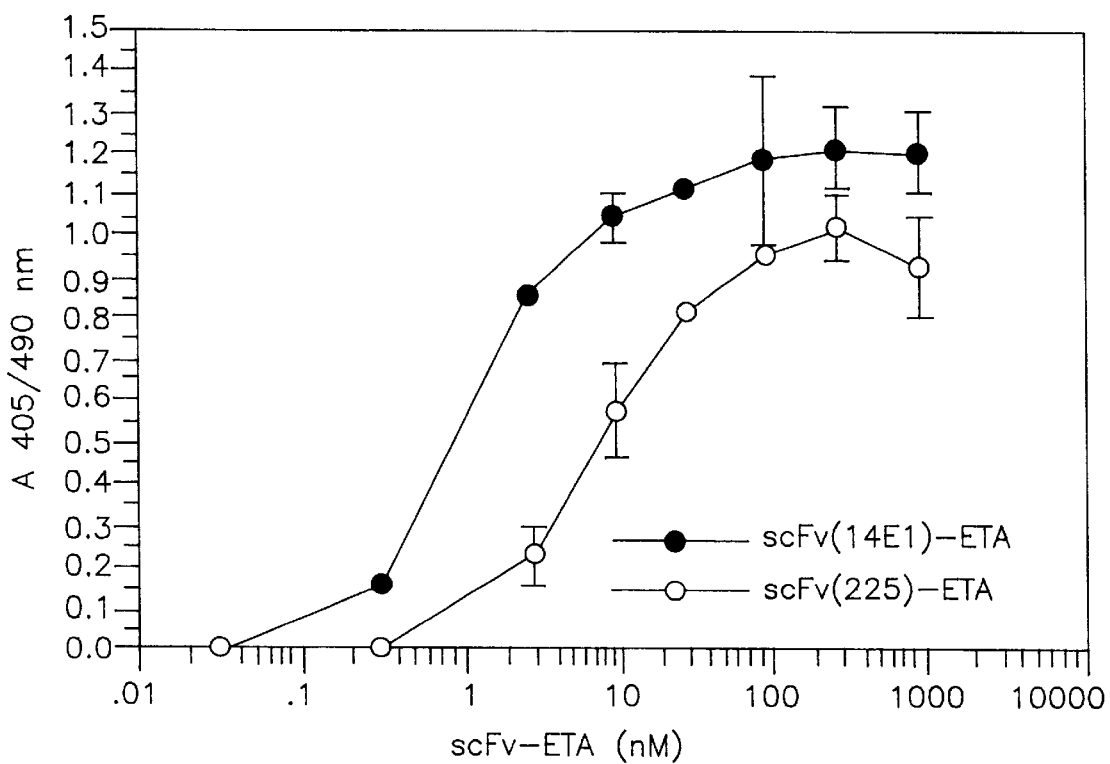
FIGS. 2A–2B Binding of scFv(14E1)-ETA and scFv(225)-ETA to recombinant extracellular domain of the EGF receptor. Immobilized extracellular domain of the EGF receptor was incubated with various concentrations of scFv (14E1)-ETA (closed circles) or scFv(225)-ETA (open circles). The amount of specifically bound protein was measured, after incubation with rabbit anti-ETA serum followed by alkaline phosphatase coupled anti-rabbit IgG and conversion of the phosphatase substrate p-nitrophenylphosphate as the absorbance at 405 nm.

The toxicity of scFv(14E1)-ETA and TGFα-ETA proteins was tested on the NIH3T3 cell lines DH-EGFR-E and DH-EΔ801-P. The cells were incubated for 40 h with various concentrations of the scFv(14E1)-ETA and TGFα-ETA proteins. As a control, the cells were also treated with the ErbB2 specific antibody-toxin scFv(FRP5)-ETA (Wels, W., Harwerth, I. M., Mueller, M., Groner, B., and Hynes, N. E. Selective inhibition of tumor cell growth by a recombinant single-chain antibody-toxin specific for the erbB-2 receptor. Cancer Res., 52: 6310-7, 1992). The relative number of viable cells in comparison to untreated controls was determined with an enzymatic assay as described in Materials and Methods. The results are shown in FIG. 7. On DH-EGFR-E cells scFv(14E1)-ETA and TGFα-ETA displayed cell killing activities in a similar range with $IC_{50}$ values of 19 ng/ml and 42 ng/ml, respectively (FIG. 7, upper left panel). In contrast, DH-EΔ801-P cells were sensitive only to high concentrations of TGFα-ETA ($IC_{50}$ of 0.7 µg/ml) but were extremely sensitive to low concentrations of scFv(14E1)-ETA ($IC_{50}$ of 0.2 ng/ml) (FIG. 2, upper right panel). As expected, none of the cell lines were sensitive to the ErbB2 specific antibody-toxin. These data show that DH-EΔ801-P cells which express EGFRvIII are approximately 3,500 times more sensitive to the scFv(14E1)-ETA antibody-toxin than to the TGFα-ETA growth factor toxin, and are approximately 100 times more sensitive to scFv(14E1)-ETA than DH-EGFR-E cells expressing fill-length human EGFR.

A similar cell killing experiment was carried out using DH-L-2 control cells which do not express human EGFR. Neither the EGFR specific toxins TGFα-ETA and scFv (14E1)-ETA nor the ErbB2 specific control protein scFv (FRP5)-ETA showed detectable cytotoxic activity on DH-L-2 cells (FIG. 2, lower panel). These data show that the activity of scFv(14E1)-ETA and TGFα-ETA proteins on DH-EΔ801-P and DH-EGFR-E NIH3T3 transfectants is dependent on the presence of the human EGFR proteins.

Example 8

Increased Sensitivity to scFv(14E1)-ETA is Dependent on EGFRvIII Expression. As shown in Example 6, DH-EGFR-E and DH-EΔ801-P cells express different levels of full-length and variant EGFR. In order to test whether the differential sensitivity of these cells to scFv(14E1)-ETA can be explained by the amount of EGFR proteins present, DH-EΔ801-5 (Hills, D., Rowlinson-Busza, G., and Gullick, W. J. Specific targeting of a mutant, activated EGF receptor found in glioblastoma using a monoclonal antibody. Int. J. Cancer, 63: 537–543, 1995), another NIH3T3 cell line expressing only low levels of EGFRvIII was analyzed. First, the relative expression levels of EGFR proteins in DH-EGFR-E, DH-EΔ801 -P, and DH-EΔ801-5 cells were determined by quantitative immunoblotting using the rabbit polyclonal antibody 12E which recognizes both, fill-length and variant EGFR (Hills, D., Rowlinson-Busza, G., and Gullick, W. J. Specific targeting of a mutant, activated EGF receptor found in glioblastoma using a monoclonal antibody. Int. J. Cancer, 63: 537–543, 1995., Gullick, W. J., Downward, J., and Waterfield, M. D. Antibodies to the autophosphorylation sites of the epidermal growth factor receptor protein-tyrosine kinase as probes of structure and function. EMBO J., 4: 2869–77, 1985). The results are not shown. Equal amounts of cell lysates from DH-EGFR-E cells, DH-L-2 control cells, and DH-EΔ801-P and DH-EΔ801-5 cells were analyzed by SDS-PAGE and immunoblotting with 12E antibody. As determined by densitometry, DH-EΔ801-P and DH-EGFR-E cells express approximately 11 times and 3.5 times higher EGFR levels than DH-EΔ801-5 cells, respectively.

The cytotoxic activity of scFv(14E1)-ETA and TGFα-ETA proteins on DH-EΔ801-5 cells was analyzed. The cells were incubated for 40 h with various concentrations of the recombinant toxins and the relative number of viable cells was determined as described above. The results are shown in FIG. 10. DH-EΔ801-5 cells were highly sensitive to scFv (14E1)-ETA ($IC_{50}$ of 2 ng/ml), but resistant to low concentrations of TGFα-ETA ($IC_{50}$>1 μg/ml). In comparison to the DH-EΔ801-P cells described above, DH-EΔ801-5 cells were 10 times less sensitive to scFv(14E1)-ETA which is in good agreement with the approximately 11 times lower EGFRvIII expression. In contrast, in comparison to DH-EGFR-E cells, DH-EΔ801-5 cells displayed 10-fold higher sensitivity to scFv(14E1)-ETA despite the 3.5 times lower level of EGFR proteins.

These results show that the sensitivity of EGFRvIII expressing cells towards scFv(14E1)-ETA is dependent on the amount of variant receptor present. However, the increased sensitivity of DH-EΔ801-P and DH-EΔ801-5 cells to scFv(14E1)-ETA in comparison to DH-EGPR-E cells cannot be explained by the total amount of EGFR proteins in these cells but is dependent on the presence of EGFRvIII.

The present invention relates to a single chain antibody-toxin, scFv(14E1)-ETA, specific for the EGF receptor and/or its variants which is based on the independently isolated Mab 14E1. This single chain antibody-toxin is well suited for targeting cells via a surface molecule such as the EGF receptor: The target-cell recognition domain binds with high affinity to its cognate receptor. Furthermore, it shows a high selectivity for EGF receptor overexpressing tumor cells and therewith minimize unwanted side effects on normal tissues that could express low levels of the target antigen, and the cytotoxic domain of the anti-tumor toxin is catalytically active so that the molecule is effective at low concentrations.

The antagonistic activity of scFv molecules could be employed directly to inhibit tumor cell growth in the absence of a cytotoxic effector domain in a way very similar to the parental antibodies. ScFv proteins of approximately 27 kDa due to their much smaller size penetrate into solid tumors much faster than intact Mabs (approximately 150 kDa). This is an advantageous especially for tumor imaging with radiolabeled compounds, where the rapid clearance of scFv molecules from the circulation of usually only several minutes is desirable.

scFv(14E1)-ETA is almost as potent as TGFα-ETA in tumor cell killing, since the antibody-toxin cannot activate the EGF receptor and is therefore limited to the passive internalization of the target antigen in order to reach the cytosol, the site of toxin activity. Since in contrast to TGFα-containing toxins scFv(14E1)-ETA lacks significant killing activity on cells expressing low EGF receptor levels, it will be more tolerable upon systemic administration and allow a broader range of therapeutic applications. ScFv (14E1)-ETA is a promising and very potent novel antitumoral reagent.

We claim:

1. A single chain polypeptide having a binding affinity for an epidermal growth factor receptor, said polypeptide comprising:
   (1) a first polypeptide segment comprising the binding portion of the heavy chain variable domain of monoclonal antibody 14E1; and
   (2) a second polypeptide segment comprising the binding portion of the light chain variable domain of monoclonal antibody 14E1.

2. A single chain polypeptide of claim 1, further comprising a polypeptide linker joining the heavy chain variable domain to the light chain variable domain.

3. A single chain polypeptide of claim 1, wherein the polypeptide linker is 15 amino acids.

4. A single chain polypeptide of claim 1, wherein the heavy chain variable domain is positioned amino-terminal to the light chain variable domain.

5. A single chain polypeptide of claim 1, further comprising a biologically-active component.

6. A single chain polypeptide of claim 1, wherein the single chain polypeptide further comprises a third polypeptide segment comprising a biologically-active component.

7. A single chain polypeptide of claim 5, wherein the biologically-active component is cytotoxic or cytostatic.

8. A single chain polypeptide of claim 7, wherein the biologically-active component is a cytotoxin.

9. A single chain polypeptide of claim 1, wherein the single chain polypeptide further comprises a third polypeptide segment comprising a cytotoxic effective portion of *Pseudomonas exotoxin A*.

10. A single chain polypeptide of claim 1, further comprising a third polypeptide segment comprising a cytotoxic or cytostatic effective portion of biologically-active component.

11. A single chain polypeptide of claim 1, which is scFv(14E1) or scFv(14E1)-ETA.

12. A single chain polypeptide of claim 1, further comprising a radiodiagnostic or radio-therapeutic agent.

13. A single chain polypeptide of claim 1, further comprising a MRI contrast agent.

14. A single chain polypeptide of claim 1, wherein the binding portion of the heavy chain variable domain comprises the sequences, SEQ ID NOs: 3,4,5 and 6, of monoclonal antibody 14E1 and the binding portion of the light chain variable domain comprises the sequences, SEQ ID NOs: 1 and 2, of the light chain variable domain of antibody 14E1.

15. A nucleic acid comprising a nucleotide sequence coding for a single chain polypeptide having a binding affinity for an epidermal growth factor receptor, said nucleic acid comprising:

(1) a first nucleotide sequence coding for a first polypeptide segment comprising the binding portion of the heavy chain variable domain of antibody 14E1; and (2) a second nucleotide sequence coding for a second polypeptide segment comprising the binding portion of the light chain variable domain of antibody 14E1.

16. A nucleic acid of claim 15, further comprising a third nucleotide sequence coding for a polypeptide linker positioning the heavy chain variable domain 5' to the light chain variable domain by a polypeptide.

17. A nucleic acid of claim 15, further comprising a third nucleotide sequence coding for a biologically-active component.

18. A nucleic acid of claim 15, wherein the biologically-active component is a cytotoxic effective portion of *Pseudomonas exotoxin A*.

19. A nucleic acid of claim 15 which codes for scFv (14E1) or scFv(14E1)-ETA.

20. A nucleic acid of claim 15 which is pSW50-14E1 or pSW202-14E1.

21. A method of imaging cells expressing an epidermal growth factor receptor comprising administering an effective amount of a compound of claim 1, wherein the single chain polypeptide comprises a radiolabeled compound or a MRI contrast agent.

22. A method of claim 21, wherein the single chain antibody is scFv(14E1).

23. A method of claim 21, wherein the cell are a breast cell carcinoma.

24. A double chain polypeptide having a binding affinity for an epidermal growth factor receptor, said polypeptide comprising:

(1) a first polypeptide segment comprising the binding portion of the heavy chain variable domain of monoclonal antibody 14E1; and (2) a second polypeptide segment comprising the binding portion of the light chain variable domain of monoclonal antibody 14E1, wherein the heavy chain variable domain is joined to the light chain variable domain by a covalent linkage extending from each of the domains.

25. A double chain polypeptide of claim 24, wherein the covalent linkage is a disulfide bond.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 357 base pairs
      (B) TYPE: nucleic acid
      (C) STRANDEDNESS: double
      (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:1:

```
CAGGTGCAGC TGCAGGAGTC TGGGGCTGAA CTGGCAAAAC CTGGGGCCTC AGTGAAGATG        60

TCCTGCAAGG CTTCTGGCTA CACCTTTACT AACTACTGGA TGCACTGGGT GACACAGAGG       120
```

```
CCTGGACAGG TGCTGGTATG GATTGGATAC ACTAATCCTA ACACTGGTTA TACTGATTTC      180

AATCAGAAGT TCAAGGACAA GGCCACATTG ACTGCAGACA AATCCTCCAG CACAGCCTAC      240

ATGCAACTGA GCGGCCTGAC ATCTGAGGAC TCTGCAGTCT ATTACTGTGC AAGAGGGGAT      300

TACTACGGCT ACGACTTTGC TTACTGGGGC CAAGGGACCA CGGTCACCGT TTCCTCT        357
```

(2) INFORMATION FOR SEQ ID NO:2:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:2:

```
Gln Val Gln Leu Gln Glu Ser Gly Ala Glu Leu Ala Lys Pro Gly Ala
1               5                   10                  15

Ser Val Lys Met Ser Cys Lys Ala Ser Gly Tyr Thr Phe Thr Asn Tyr
            20                  25                  30

Trp Met His Trp Val Thr Gln Arg Pro Gly Gln Val Leu Val Trp Ile
        35                  40                  45

Gly Tyr Thr Asn Pro Asn Thr Gly Tyr Thr Asp Phe Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Gly Leu Thr Ser Glu Asp Ser Ala Val Tyr Tyr Cys
            85                  90                  95

Ala Arg Gly Asp Tyr Tyr Gly Tyr Asp Phe Ala Tyr Trp Gly Gln Gly
            100                 105                 110

Thr Thr Val Thr Val Ser Ser
        115
```

(2) INFORMATION FOR SEQ ID NO:3:

(i) SEQUENCE CHARACTERISTICS:
        (A) LENGTH: 318 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:3:

```
GACATCCAGC TGACCCAGTC TCCAGCCATC CTGTCTGTGA GTCCAGGAGA AAGAGTCAGT      60

TTCTCCTGCA GGGCCAGTCA GAGCATTGGC ACAAATATAC ACTGGTATCA GCAAAGAACA     120

AATGGTTCTC CAAGGCTTCT CATAAAGTAT GCTTCTGAGT CTATCTCTGG GATCCCTTCC     180

AGGTTTAGTG GCAGTGGATC AGGGACAGAT TTTACTCTTA GCATCAACAG TGTGGAGTCT     240

GCAGATATTG CAGATTATTA CTGTCAACAA AGTGATAGCT GGCCAACCAC GTTCGGTGCT     300

GGGACAAAGC TCGAGATT                                                   318
```

(2) INFORMATION FOR SEQ ID NO:4:

(i) SEQUENCE CHARACTERISTICS:
        (A) LENGTH: 106 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:4:

```
Asp Ile Gln Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Ala Asp Ile Ala Asp Tyr Tyr Cys Gln Gln Ser Asp Ser Trp Pro Thr
                85                  90                  95

Thr Phe Gly Ala Gly Thr Lys Leu Glu Ile
                100                 105
```

(2) INFORMATION FOR SEQ ID NO:5:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:5:

```
GACATTGAGC TCACCCAGTC TCCATCCTCC CTGACTGTGG CAGCAGGAGA GAAGGTCACT      60

ATGAGCTGCA AGTCCAGTCA GAGTCTCTTA GCTAGTGGCA ACCAAAATAA CTACTTGGCC     120

TGGCACCAGC AGAAACCAGG ACGATCTCCT AAAATGCTGA TAATTTGGGC ATCCACTAGG     180

GTTTCTGGAG TCCCTGATCG CTTCATAGGC AGTGGATCTG GGACGGATTT CACTCTGACC     240

ATCAACAGTG TGCAGGCTGA AGATCTGGCT GTTTATTACT GTCAGCAGTC CTACAGCGCT     300

CTCACGTTCG GTGCTGGCAC CAAGCTGGAA ATC                                  333
```

(2) INFORMATION FOR SEQ ID NO:6:

(i) SEQUENCE CHARACTERISTICS:
        (A) LENGTH: 111 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:6:

```
Asp Ile Glu Leu Thr Gln Ser Pro Ser Ser Leu Thr Val Ala Ala Gly
1               5                   10                  15

Glu Lys Val Thr Met Ser Cys Lys Ser Ser Gln Ser Leu Leu Ala Ser
                20                  25                  30

Gly Asn Gln Asn Asn Tyr Leu Ala Trp His Gln Gln Lys Pro Gly Arg
            35                  40                  45

Ser Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Leu Thr Phe Gly Ala Gly Thr Lys Leu Glu Ile
            100                 105                 110
```

(2) INFORMATION FOR SEQ ID NO:7:

(i) SEQUENCE CHARACTERISTICS:
        (A) LENGTH: 720 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:7:

```
CAGGTGCAGC TGCAGGAGTC TGGGGCTGAA CTGGCAAAAC CTGGGGCCTC AGTGAAGATG      60
TCCTGCAAGG CTTCTGGCTA CACCTTTACT AACTACTGGA TGCACTGGGT GACACAGAGG     120
CCTGGACAGG TGCTGGTATG GATTGGATAC ACTAATCCTA ACACTGGTTA TACTGATTTC     180
AATCAGAAGT TCAAGGACAA GGCCACATTG ACTGCAGACA AATCCTCCAG CACAGCCTAC     240
ATGCAACTGA GCGGCCTGAC ATCTGAGGAC TCTGCAGTCT ATTACTGTGC AAGAGGGGAT     300
TACTACGGCT ACGACTTTGC TTACTGGGGC CAAGGGACCA CGGTCACCGT TCCTCTGGC      360
GGTGGCGGTT CTGGTGGCGG TGGCTCCGGC GGTGGCGGTT CTGACATCCA GCTGACCCAG     420
TCTCCAGCCA TCCTGTCTGT GAGTCCAGGA GAAAGAGTCA GTTTCTCCTG CAGGGCCAGT     480
CAGAGCATTG GCACAAATAT ACACTGGTAT CAGCAAAGAA CAAATGGTTC TCCAAGGCTT     540
CTCATAAAGT ATGCTTCTGA GTCTATCTCT GGGATCCCTT CCAGGTTTAG TGGCAGTGGA     600
TCAGGGACAG ATTTTACTCT TAGCATCAAC AGTGTGGAGT CTGCAGATAT TGCAGATTAT     660
TACTGTCAAC AAAGTGATAG CTGGCCAACC ACGTTCGGTG CTGGGACAAA GCTCGAGATT     720
```

(2) INFORMATION FOR SEQ ID NO:8:

(i) SEQUENCE CHARACTERISTICS:
        (A) LENGTH: 240 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:8:

| | | | | | | | | | | | | | | |
|---|---|---|---|---|---|---|---|---|---|---|---|---|---|---|
|Gln|Val|Gln|Leu|Gln|Glu|Ser|Gly|Ala|Glu|Leu|Ala|Lys|Pro|Gly|Ala|
|1| | | |5| | | | |10| | | | |15| |

Ser Val Lys Met Ser Cys Lys Ala Ser Gly Tyr Thr Phe Thr Asn Tyr
            20                  25                  30

Trp Met His Trp Val Thr Gln Arg Pro Gly Gln Val Leu Val Trp Ile
        35                  40                  45

Gly Tyr Thr Asn Pro Asn Thr Gly Tyr Thr Asp Phe Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Gly Leu Thr Ser Glu Asp Ser Ala Val Tyr Tyr Cys
                85                  90                  95

Ala Arg Gly Asp Tyr Tyr Gly Tyr Asp Phe Ala Tyr Trp Gly Gln Gly
            100                 105                 110

Thr Thr Val Thr Val Ser Ser Gly Gly Gly Ser Gly Gly Gly Gly
            115                 120                 125

Ser Gly Gly Gly Gly Ser Asp Ile Gln Leu Thr Gln Ser Pro Ala Ile
    130                 135                 140

Leu Ser Val Ser Pro Gly Glu Arg Val Ser Phe Ser Cys Arg Ala Ser
145                 150                 155                 160

Gln Ser Ile Gly Thr Asn Ile His Trp Tyr Gln Gln Arg Thr Asn Gly
            165                 170                 175

Ser Pro Arg Leu Leu Ile Lys Tyr Ala Ser Glu Ser Ile Ser Gly Ile
            180                 185                 190

Pro Ser Arg Phe Ser Gly Ser Gly Ser Gly Thr Asp Phe Thr Leu Ser
            195                 200                 205

Ile Asn Ser Val Glu Ser Ala Asp Ile Ala Asp Tyr Tyr Cys Gln Gln
            210                 215                 220

Ser Asp Ser Trp Pro Thr Thr Phe Gly Ala Gly Thr Lys Leu Glu Ile
225                 230                 235                 240

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:9:

AGGTSMARCT GCAGSAGTCW GG                                      22

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:10:

TGAGGAGACG GTGACCGTGG TCCCTTGGCC CC                                32

(2) INFORMATION FOR SEQ ID NO:11:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:11:

GCGACCTTGC ACGCGTAGAC ATTGAGCTCA CCCAGTCTCC A                      41

(2) INFORMATION FOR SEQ ID NO:12:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:12:

CGCTACAATA GCGGCCGCTA CCGTCCGTTT GATTTCCAGC TTGGTGCC               48

(2) INFORMATION FOR SEQ ID NO:13:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:13:

CGCTACATTA GCGGCCGCTA CCGTCCGTTT CAGCTCCAGC TTGGTCCC               48

(2) INFORMATION FOR SEQ ID NO:14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:14:

TGAGGAGACG GTGACCGTGG TCCCTTGGCC CCAG                              34

(2) INFORMATION FOR SEQ ID NO:15:

(i) SEQUENCE CHARACTERISTICS:
    (A) LENGTH: 34 base pairs
    (B) TYPE: nucleic acid
    (C) STRANDEDNESS: single
    (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:15:

ATTATAAGCT TCAGGTSMAR CTGCAGSAGT CWGG            34

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:16:

TTAGATCTCT AGAAKCTCGA GYTTKGTSC                  29

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:17:

GACATTCAGC TGACCCAGWC TSC                        23